(12) United States Patent
Behrens et al.

(10) Patent No.: US 8,071,094 B2
(45) Date of Patent: Dec. 6, 2011

(54) ANTI-IDIOTYPIC ANTIBODY NEUTRALIZING THE INHIBITOR ACTIVITY OF A FACTOR VIII INHIBITOR ANTIBODY

(75) Inventors: Christian Behrens, Palaiseau (FR); Marc Jacquemin, Sart-Bernard (BE); Jean Guy Gilles, Brussels (BE); Jean-Marie Saint-Remy, Grez-Doiceau (BE)

(73) Assignee: Laboratoire Francais du Fractionement Et des Biotechnologies, Les Ulis (FR)

( * ) Notice: Subject to any disclaimer, the term of this patent is extended or adjusted under 35 U.S.C. 154(b) by 19 days.

(21) Appl. No.: 11/458,373

(22) Filed: Jul. 18, 2006

(65) Prior Publication Data
US 2007/0065425 A1    Mar. 22, 2007

(30) Foreign Application Priority Data
Aug. 4, 2005 (FR) .................................. 05 08320

(51) Int. Cl.
A61K 39/395 (2006.01)
C07H 21/04 (2006.01)
C07K 14/42 (2006.01)
C12N 5/06 (2006.01)

(52) U.S. Cl. ............... 424/131.1; 530/387.2; 536/23.53
(58) Field of Classification Search ............... 424/131.1; 530/387.2; 536/23.53
See application file for complete search history.

(56) References Cited

U.S. PATENT DOCUMENTS

| 5,530,101 | A  | * | 6/1996  | Queen et al. | ............... | 530/387.3 |
| 7,364,735 | B1 | * | 4/2008  | Voorberg et al. | ......... | 424/145.1 |
| 2006/0239998 | A1 | * | 10/2006 | Gilles et al. | ................ | 424/131.1 |
| 2008/0160015 | A1 | * | 7/2008  | Gilles et al. | ................ | 424/131.1 |

FOREIGN PATENT DOCUMENTS
WO   WO 2004/014955   2/2004

OTHER PUBLICATIONS

Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Casset et al. ((2003) BBRC 307, 198-205).*
Holm et al (Molec. Immunol. (2007) 44, 1075-1084).*
MacCallum et al. (J. Mol. Biol. (1996) 262, 732-745).*
Ananyeva et al. (Blood Coagul. Fibrinolysis 15(2):109-124 (Mar. 2004)).*
Scandella et al. (Blood 82:1767 (1993)).*
Fundamental Immunology 242 (William E. Paul, M.D. ed., 3d ed. 1993).*
ATCC search output for: IR983F, PERC6, CHO-Lec10, CHO-Lec1, CHO-Lec13 and Sp2/0-Ag 14, (Nov. 30, 2007).*
Janeway et al. (Immunobiology, third edition, Garland Press, 1997, pp. 3:7-11).*
Rudikoff et al (Proc Natl Acad Sci USA 79 p. 1979 (1982)).*
Jones, Peter T. et al., "Replacing the complementanty-deterimining regions in a human antibody with those from a mouse", Nature vol. 321, 1986, pp. 522-525.
Riechmann, Lutz et al., "Reshaping human antibodies for therapy", Nature vol. 332, 1988, 323-327.
Madec, Anne-Marie et al., "Four IgG anti-islet human monoclonal antihodies isolated from a type 1 diabetes patient recognize distinct epitopes of glutamic acid decarboxylase 65 and are somatically mutated", The Journal of Immunology, vol. 156, 1996, 3541-3649.
Sato, Koh et al., "Reshaping a human antibody to inhibit the interleukin 6-dependent tumor cell growth", Cancer Research, vol. 53, 1993, 651-868.
Giles, Jean Guy et al., "In vivo neutralization of a C2 domain-specific human anti-factor VIII inhibitor by an anti-adiotypic antibody", Blood, vol. 103, 2004 2617-2823.
Lubahn, Beth C. et al., "Characterization of a monoclonal anti-idiotype antibody to human anti-factor VIII antibodies", Proc. Natl. Academy of Science, vol. 87, 1990, 8232-8236.
Healy, John F. et al., "Residues 484-508 contain a major determinant of the inhibitory epitope in the A2 domain of human factor VIII", The Journal of Biological Chemistry, vol. 270, 1995, 14505-14509.
Dietrich, Gilles et el., "A monoclonal anti-idiotypic antibody against the antigen-combining site of anti-factor VIII autoantibodies defines an idiotope that is recognized by normal human polyspecific immunoglobulins for therapeutic use (IVIg)", Journal of Autoimmunity, vol. 3, 1990, 647-557.
Gilles, Jean Guy G. et al., "Antibodies to idiotypes of human monoclonal anti-factor VIII (FVIII) antibodies neutralise their inhibitory activity", Transfusion iVtedicine II, Abstract No. 2048, p. 460a, XP001109476, Dec. 1999.
Saint-Remy, Jean Marie et al., "Anti-Idiotybio Antibodies: From Regulation to Therapy of Factor VIII Innibitors" Vox Sang 1999;77(suppl 1):21-24.
Lollar, Pete et al., "Inhibition of Human Factor Villa by Anti-A2 Subunit Antibodies" J. Clin. Invest vol. 93, Jun. 1994, pp. 2497-2504.
Fay, Philip et al., "Model for the Factor Villa-dependent Decay of the Intrinsic Factor Xase" J. Biol. Chem. vol. 271, No. 11, 1996, pp. 6027-5032. Morrison, Sherie el al., "Chimeric human antibody molecules: Mouse antigen-binding domains with human constant region domains" Proc. Nat. Acad. Sci. USA vol. 81, pp, 6851-6856, Nov. 1984.
Wood et al.,"Expression of active human factor VIII from reciombinant DNA clones," Nature (1984) 312:330-337.
Gilles J.G. et al., "Anti-Factor VIII Antibodies of Hemophiliac Patients Are Frequently Directed Towards Nonfunctional Determinants and Do Not Exhibit Isotypic Restriction," (1993) Blood; vol. 82, No. 8, pp. 2452-2461.
Jarvis et al., "Induction of Human Factor VIII Inhibitors in Rats by Immunization with Human Recombinant Factor VIII: a Small Animal Model for Humans with Higher Responder Inhibitor Phenotype" Thrombosis and Haemostasis Feb. 1996; 75(2)318-25.
Jacquemin, Marc et al., "A human antibody directed to the factor VIII C1 domain inhibits factor VIII cofactor activity and binding to von Willebrand factor" (2000) Blood 95:155-163.
Jaquemin, Marc et al., "Mechanism and Kinetics of Factor VIII Inactivation: Study With an IgG4 Monoclonal Antibody Derived From a Hemophilia A Patient With Inhibitor," Blood 1995 Jul. 15: 92(496-506).
Ananyeva, Natalya et al., "inhibitors in homoohilla A: mechanisms of inhibition, management and perspectives," (2004) Blood Coagulation and Fibrinolysis. Mar: 15(2)109-124.

* cited by examiner

*Primary Examiner* — Lynn Bristol
(74) *Attorney, Agent, or Firm* — Birch, Stewart, Kolasch & Birch, LLP

(57) ABSTRACT

The present invention is related to a monoclonal anti-idiotypic antibody directed against a Factor VIII inhibitor antibody binding to the domain A2 of Factor VIII, and to a cell line producing this monoclonal anti-idiotypic antibody, to the use of this monoclonal anti-idiotypic antibody as drug, and more particularly, to its use for the manufacturing of a drug to be used for the treatment of haemophilia A.

13 Claims, 6 Drawing Sheets

Fig. 8

ANTI-IDIOTYPIC ANTIBODY NEUTRALIZING THE INHIBITOR ACTIVITY OF A FACTOR VIII INHIBITOR ANTIBODY

PRIOR ART AND INTRODUCTION

The present invention is related to an anti-idiotypic monoclonal antibody directed against a Factor VIII inhibitor antibody binding to the domain A2 of Factor VIII, and to a cell line producing this anti-idiotypic monoclonal antibody, to the use of this anti-idiotypic monoclonal antibody as drug, and more particularly to its use for the manufacturing of drugs for the treatment of haemophilia A.

Haemophilia A is a hereditary disease due to an anomaly of the chromosome X, which is expressed in the affected person by an inability to coagulate. This disease is the result of mutations on the gene of a protein taking part in the coagulation, the Factor VIII (FVIII), which determine either a total absence of Factor VIII in the blood, or a partial deficit thereof.

Haemophilia A is the most common of insufficiencies affecting the blood coagulation: in France 1 male out of 5000 is affected, that is 80% of patients are suffering from haemophilia. The other type of haemophilia, haemophilia B, affects 20% of patients suffering from haemophilia; it is due to the deficiency of an other clotting factor, Factor IX.

Present treatment of heamophilia (type A or B) consists of intravenous administration of the deficient or absent clotting Factor. In France, the Factor VIII for the treatment of haemophiliacs is available in form of blood derived drugs provided by the Laboratoire Français du Fractionnement et des Biotechnologies (LFB) or by international pharmaceutical laboratories, as well as in form of recombinant drugs prepared by genetic engineering methods. Indeed, the DNA encoding the Factor VIII was isolated and expressed in mammal cells (Wood et al., Nature (1984) 312: 330-337), and its amino acid sequence derived from the cDNA.

The secreted Factor VIII (FVIII) is a glycoprotein with a molecular weight of 300 Kda (2332 amino acids), which plays a key role in the activation of the coagulation intrinsic pathway. The inactive FVIII consists of six regions: A1 (residues 1-372), A2 (residues 373-740), B (residues 741-1648), A3 (residues 1649-2019), C1 (residues 2020-2172) and C2 (residues 2173-2332), from the N-terminal extremity to the C-terminal extremity. After being secreted, the FVIII interacts with the von Willebrand Factor (vWF), which protects the FVIII against plasma proteases. The FVIII dissociates from the vWF upon cleavage by thrombin. This cleavage results in the elimination of the domain B and in the formation of a heterodimer. FVIII circulates in the plasma in this form. This heterodimer consists of a heavy chain (A1, A2) and of a light chain (A3, C1, C2).

When FVIII is infused to a haemophiliac patient, it is binding to the von Willebrand Factor in the blood circulation of the patient. The activated Factor VIII acts as a co-factor of the activated Factor IX, accelerating the conversion of Factor X in active Factor X. The activated Factor X converts the prothrombin in thrombin. Then the thrombin converts the fibrinogen in fibrin, followed by a clot formation.

The major problem encountered with administration of Factor VIII, is the appearance of antibodies directed against the Factor VIII in the patient, referred to as <<inhibiting antibodies>>. These antibodies neutralize the Factor VIII procoagulant activity, which is inactivated as soon as infused. Thus, the administered clotting factor is destructed before the bleeding could have been stopped, which is a serious complication of haemophilia, turning out the treatment to be ineffective. Further, some genetically non haemophiliac patients may develop inhibitors against the endogenous Factor VIII: this is an acquired haemophilia.

Studies have shown that the anti-Factor VIII immune response is of polyclonal IgG type, belonging for the most part to the sub-class IgG4 and IgG1, and seldom to IgG2. IgG3 are never represented. The light chain is often of Kappa type. The overrepresentation of IgG4 is more pronounced with the heamophiliacs having an inhibitor established since long-time. The domains C2 and A2 of the FVIII molecule are the favored targets of the immune response, although in some cases, antibodies to the domain A3 are detected. When plasma of haemophiliac patients is passed on an immunoadsorption column with immobilized FVIII, it is possible to purify the total amount of anti-FVIII antibodies. The harvested amounts are often higher than 100 µg per 10 mg of total IgGs (Gilles J G et al. (1993) Blood; 82 : 2452-2461). An animal model was developed with the aim to study the formation of Factor VIII inhibitors; rats immunized with human recombinant Factor VIII show a rapid immune response of polyclonal type (Jarvis and al. Thromb Haemost. 1996 Feb. 75(2):318-25). There exists a number of mechanisms of the anti-Factor VIII antibodies interference with the Factor VIII function including the interference in the proteolytic cleavage of Factor VIII and in the interaction of Factor VIII with different partners, such as von Willebrand Factor (vWF), the phospholipids (PL), the Factor IX, activated Factor X (FXa) or APC (Activated Protein C).

Several treatments allowing to attenuate the consequences of this immune response are available, such as for example treatments implying desmopressin, which is a synthetic hormone stimulating the production of Factor VIII, agents promoting the coagulation, such as concentrates of prothrombin complexes or concentrates of activated prothrombin complexes, recombinant Factor VIIa, plasmapheresis and infusions of large or intermediary amounts of Factor VIII. Nevertheless, these methods are very expensive and of low efficiency.

Because of the complexity of the in vivo analysis of this immune polyclonal response, monoclonal antibodies directed against certain domains of Factor VIII were isolated by research teams. Thus, a human monoclonal antibody of IgG4kappa type, LE2E9, was isolated. This antibody is directed against the domain C1 of Factor VIII and inhibits the Factor VIII cofactor activity and its binding to the von Willebrand Factor (Jacquemin et al. (2000) Blood 95:156-163). In the same way, a human monoclonal antibody directed against the domain C2 of Factor VIII, referred to as BO2C11 (IgG4kappa), produced from a repertory of memory B cells of a patient suffering from haemophilia A with inhibitors, was isolated (Jacquemin and al. Blood 1998 Jul. 15; 92 (2):496-506). BO2C11 recognizes the domain C2 of Factor VIII, and inhibits its binding to von Willebrand Factor and to phospholipids. It inhibits completely the procoagulation activity of the native and active Factor VIII. A further example of monoclonal antibody is the BOIIB2 antibody directed against the domain A2 of Factor VIII. The BOIIB2 antibody inhibits 99% of the Factor VIII activity. By binding to the domain A2, it can interfere and inhibit the binding of FIXa which contains a low affinity binding site within this region of FVIII and, from that moment, inhibits the enzyme activity of FIXa. The second conceivable way of action is its interference in the equilibrium between the hetero-dimer form (A2:A1 and A3:C1:C2) of FVIII and the hetero-trimer form (A2 and A1 and A3:C1:C2) of FVIII accelerating the dissociation of the domain A2 of these complexes, making them non functional. (Ananyeva N M et al, (2004), Blood Coagul Fibrinolysis. March 15(2):109-24. Review).

Thanks to these novel tools, a further, more recent strategic struggle against the Factor VIII inhibitor antibodies, considers the administration of anti-idiotypic antibodies (antibodies having the capacity to interact with the variable region of other antibodies) neutralizing the inhibitor antibodies (Saint-Rémy J M et al, (1999) Vox Sang; 77 (suppl 1): 21-24). A mouse anti-idiotypic antibody, the 14C12, disclosed in the document WO 2004/014955, neutralizes in vivo, in a dose-dependent manner, the inhibitor properties of the anti-Factor VIII target antibody (BO2C11 monoclonal antibody), which is directed against the domain C2 of Factor VIII. Nevertheless, the anti-Factor VIII immune response is polyclonal, and the Factor VIII inhibitor antibodies developed in a patient are not necessarily directed against the domain C2 of Factor VIII. A treatment consisting of administration of sole 14C12 antibodies could neutralize only partially the anti-Factor VIII immune response developed in the patient.

A further dominant category of Factor VIII inhibitor antibodies found in patients suffering from haemophilia A, which developed inhibitors, consists of inhibitor antibodies directed against the domain A2 of Factor VIII. The domain A2 is a domain of 43 kD. Its function is yet not well known, but it was shown that inhibitory antibodies directed against the domain A2 of Factor VIII inhibit the function of Factor VIIIa by inhibition of the conversion of the complex FXase/FX in the state of transition (Lollar et al. J Clin Invest. 1994 June; 93(6):2497-504, Fay et al. J Biol. Chem. 1996; 271(11): 6027-6032).

Thus, the inhibitor antibodies directed against the domain A2 of Factor VIII are very important in the immune response directed against the Factor VIII, this response is mixed and uses in a predominant manner the intervention of antibodies directed against the domain A2 and antibodies directed against the domain C2 of Factor VIII. Now, no tool exists allowing to neutralize inhibitor antibodies directed against the domain A2 of Factor VIII.

Therefore the Applicant at first attempted to develop a novel tool for treatment of haemophilia A allowing to neutralize the inhibitor antibodies directed against the domain A2 of Factor VIII. Subsequently, the Applicant attempted to develop a novel tool permitting to neutralize the inhibitory effect of the major part of inhibitor antibodies developed in a patient suffering from haemophilia A with inhibitors.

Thus, the Applicant has manufactured a novel anti-idiotypic antibody directed against a Factor VIII inhibitor antibody, this inhibitor antibody is binding to the domain A2 of Factor VIII. Surprisingly, the Applicant noticed that the use of the anti-idiotypic antibody according to the invention simultaneously with an anti-idiotypic antibody directed against an inhibitor binding to the domain C2 of Factor VIII, has a neutralizing effect on the inhibitor effect of the anti-Factor VIII immune response, and particularly, on the immune response induced by the inhibitor antibodies directed against the domain A2 and by the inhibitor antibodies directed against the domain C2 of Factor VIII.

DETAILED DESCRIPTION OF THE INVENTION

Thus, a first subject matter of the invention relates to a Factor VIII monoclonal anti-idiotypic antibody directed against a human inhibitor antibody, the inhibitor antibody being directed against the domain A2 of Factor VIII.

It is understood that the term Factor VIII <<inhibitor antibodies>> or <<inhibitors>> refers to antibodies which inhibit the Factor VIII procoagulant activity, especially by binding to it, and particularly an anti-Factor VIII antibody, the epitope of which is located on the Factor VIII. Advantageously, the antibody of the invention is capable to neutralize at least 50%, advantageously at least 60%, and still more advantageously at least 70%, 80%, 90%, 99% or 100% of the coagulation inhibiting activity of the inhibitor antibodies directed against the domain A2 of Factor VIII, targets of the monoclonal anti-idiotypic antibodies of the invention. This capacity to neutralize the coagulation inhibiting activity of the inhibitor antibodies can be determined by measuring the Factor VIII activity in presence of an inhibitor antibody and of an anti-idiotypic antibody in an assay such as the <<factor VIII chromogenic test>> (Jacquemin et al. (1998) Blood 92, 494-506).

The anti-idiotypic monoclonal antibody of the invention can be of human or animal origin. Further, it can be obtained in different ways. For example, cells producing the anti-idiotypic antibodies can be obtained from peripheral blood lymphocytes of patients with anti-Factor VIII inhibitor antibodies or from healthy individuals. These cells can be immortalized by means of well known techniques to those skilled in the art, and selected with regard to the capacity of the produced anti-idiotypic antibodies to neutralize the inhibitor antibodies directed against the Factor VIII. A further means to produce the anti-idiotypic monoclonal antibody of the invention is the immunization of animals, advantageously mice, by injection of Factor VIII inhibitor antibodies directed against the domain A2 of Factor VIII, the fusion of spleen lymphocytes with a myeloma cell line, advantageously of mice myeloma, followed by identification and cloning of cell cultures producing the anti-idiotypic antibodies directed against the Factor VIII inhibitor antibodies.

In a particular aspect of the invention, the anti-idiotypic antibody of the invention is directed against inhibitor antibodies of which variable domain of the heavy chain presents similarities with the germ line DP-71. Such inhibitor antibodies can be obtained from humans (for example from sera of patients having inhibitor antibodies) or other animal like mice, horses, goats, non human primates, this enumeration is not limiting, by immunization with Factor VIII or fragments derived from Factor VIII, and more particularly, with a fragment comprising the whole or only a part of the domain A2.

Advantageously, the target inhibitor antibody of the anti-idiotypic antibody of the invention recognizes the epitope located between Factor VIII amino acids 484 to 508. More precisely, the recognized epitope is a conformational epitope comprising the residues 484 to 508 and the glutamic acid residues 389, 390 and 391 of Factor VIII. Indeed, the domain A2 of Factor VIII comprises the Factor VIII amino acids 373-740. This domain is involved in the recognition of the Factor VIII by the Factor IX, which binds to the domains A2 and A3 of Factor VIII, and in the inactivation of Factor VIII, this domain being one of the principal epitopes recognized by the inhibitor antibodies.

Preferably, the target inhibitor antibody of the anti-idiotypic antibody of the invention is the BOIIB2 antibody, deposited on Aug. 4, 2005, to the Belgian Coordinated Collections of Microorganisms (Technologiepark 927, Gent-Zwijnaarde B-9052, Belgium), under the number LMBP 6422CB. The BOIIB2 antibody is a human monoclonal antibody IgG4 directed against the domain A2 of Factor VIII initially produced from lymphocytes of a patient with severe haemophilia A having a high rate of inhibitors. This antibody belongs to the sub-class IgG4 and is derived from the germ line DP-71. The epitope recognized on the Factor VIII is located on the level of the residues 484 to 508. More precisely, the BOIIB2 antibody recognizes the conformational epitope comprising the residues 484 to 508 and the glutamic acid residues 389, 390 and 391. The BOIIB2 antibody inhibits the Factor VIII activity to 99% by interfering with the function of the tenase complex either by inhibiting the binding of FIXa and/or of FX to the tenase complex, or by accelerating the dissociation of the domain A2. In a particular aspect of the invention, the variable region of each of the light chains of the monoclonal anti-idiotypic antibody of the invention is encoded by a nucleic acid sequence having at least 70% identity with the nucleic acid sequence SEQ ID NO: 2, and the variable region of each of the heavy chains of the monoclonal anti-idiotypic antibody is encoded by a nucleic acid sequence having at least 70% identity with the nucleic acid sequence SEQ ID NO: 1. In a particularly advantageous way, the sequence identity is at least 80%, and preferably an identity at least from 95 to 99%. The percentage of identity is calculated by aligning 2 sequences to be compared and by counting the number of positions having an identical nucleotide, this number is divided by the total number of nucleotides of the sequence. The genetic code redundancy may be at the origin of the fact that the same amino acid can be encoded by several triplets of different nucleotides. In any case, these sequence differences do not affect at all the affinity of the monoclonal antibody to its target, neither its capacity to neutralize the inhibitor activity of the target inhibitor antibodies.

In a preferred aspect of the invention, the variable region of each of the light chains of the monoclonal anti-idiotypic antibody is encoded by the nucleic acid sequence SEQ ID NO: 2, and the variable region of each of the heavy chains of monoclonal anti-idiotypic antibody is encoded by the nucleic acid sequence SEQ ID NO: 1.

Advantageously, the peptide sequence of each of the variable regions of the light chains of antibodies of the invention is a sequence having at least 70% identity, and in a advantageous way at least 80% or 90%, and in a still more advantageous way at least 99% identity with the sequence SEQ ID NO: 4.

Advantageously, the peptide sequence of each of the variable regions of the heavy chains of the antibody of invention is a sequence having at least 70% identity, and advantageously at least 80% or 90%, and in a still more advantageous way at least 99% identity with the sequence SEQ ID NO: 3.

In a particularly advantageous way, the peptide sequence of each of the light chains of the antibody of invention is a sequence having at least 70% identity, and more advantageously, at least 80% or 90%, in a still more advantageous way at least 99% identity with the sequence SEQ ID NO: 4, and the peptide sequence of each of the heavy chains of the antibody of invention is a sequence having at least 70% identity, and advantageously at least 80% or 90%, and in a still more advantageous way at least 99% identity with the sequence SEQ ID NO: 3.

Preferably, the peptide sequence of each of the light chains of antibody of invention is the sequence SEQ ID NO: 4.

Preferably, the peptide sequence of each of the light chains of the antibody of invention is the sequence SEQ ID NO: 3.

The peptide sequence derived from the SEQ ID NO: 2 is the sequence SEQ ID NO: 4 and the peptide sequence derived from the sequence SEQ ID NO: 1 is the sequence SEQ ID NO: 3. Preferably, the variable region of each of the light chains of the monoclonal anti-idiotypic antibody of invention has the peptide sequence SEQ ID NO: 4 and the variable region of each of the heavy chains of the monoclonal anti-idiotypic antibody of invention has the peptide sequence SEQ ID NO: 3.

The antibody of invention is also understood as any modified antibody satisfying the characteristics of the invention, wherein one or more amino acids is(are) substituted or deleted. Such a substitution or deletion may be located in any position in the molecule. In the case that more amino acids were substituted or deleted, any substitution or deletion combination may be considered. Such alterations of the variable regions sequence of the antibody of invention may be carried out to increase the number of residues liable to get in contact between the anti-idiotypic antibody of the invention and the target inhibitor antibody.

In an embodiment of the invention, the anti-idiotypic antibody is a mouse antibody.

Advantageously, this mouse monoclonal anti-idiotypic antibody is a IgG1kappa.

Preferably, the monoclonal antibody of the invention is a chimeric antibody. A <<chimeric antibody>> is understood to be an antibody, the variable regions of the light chains and heavy chains of which belong to a different species of the constant regions of the light chains and heavy chains. Thus, the antibody of the invention has, moreover, the constant regions of its light and heavy chains belonging to a non murine species. To this respect, all mammal non murine families and species are liable to be used, and particularly human, monkey, murides (except mouse), the Suidae, the Bovidae, members of the horse family, the Felidae, the Canidae, for example, and birds as well.

The chimeric antibodies of the invention can be made by means of standard techniques of the recombinant DNA, known to those skilled in the art, and more particularly by means of <<chimeric>> antibodies construction techniques described, for example by Morrison et al., Proc. Natl. Acad. Sci. U.S.A., 81, pp. 6851-55 (1984), wherein the technology of the recombinant DNA is used to replace the constant region of a heavy chain and/or the constant region of a light chain of an antibody derived from a non human mammal with the corresponding regions of a human immunoglobulin.

In a particular aspect of the invention, the antibody of the invention is a human hybrid antibody, i.e. a chimeric antibody, the constant part of which is human. This embodiment of the invention allows to reduce the antibody immunogenicity in human beings and by the same, to improve its efficiency upon administration as therapeutic to human beings.

Advantageously, the antibody of the invention is a humanized antibody. Such an antibody can be obtained by association of one or more CDR region(s) (complementarity determining region) of a monoclonal antibody of a non human species with the variable human framework regions (highly conserved regions of the variable regions), such a process for obtaining is taught in the state of the art (Jones et al. Nature (1986) 321:522); Riechmann and al., Nature (1988) 332: 323).

Advantageously, the monoclonal anti-idiotypic antibody of the invention is the 30D1 antibody produced by the 30D1 hybridoma deposited on Jun. 14, 2005, under the accession number CNCM I-3450 at the Collection Nationale de Cultures de Microorganismes (CNCM), the address of which is INSTITUT PASTEUR, 25 rue du Docteur Roux, F-75724 PARIS Cedex 15. The variable region of each of the light chains of the 30D1 monoclonal anti-idiotypic antibody is encoded by the nucleic acid sequence SEQ ID NO: 2, and the variable region of each of the heavy chains of the 30D1 monoclonal anti-idiotypic antibody is encoded by the nucleic acid sequence SEQ ID NO: 1. The method for obtaining the 30D1 hybridoma is described in the Part <<Examples>> of this document.

It is understood that by "monoclonal anti-idiotypic antibody of the invention" is meant any antibody comprising fragments of the 30D1 antibody, and more particularly, any antibody comprising the variable region of the light chain and/or the variable region of the heavy chain of the 30D1 antibody, or any fragment of the variable region of the light chain and/or the variable region of the heavy chain of the 30D1 antibody. <<Fragments>> are understood as referring to a fragment F(ab')2 or a fragment Fab' or a fragment Fab or a region CDR (complementarity determining region) or any modified version of any one of these fragments or region.

In a particular embodiment of the invention, the monoclonal anti-idiotypic antibody of the invention is a fragment F(ab')2 or a fragment Fab' or a fragment Fab or a region CDR (complementarity determining region) or any modified version of any one of these fragments or region. The enzyme digestion of immunoglobulins by papain generates 2 identical fragments referred to as <<fragment Fab>> (Fragment Antigen Binding), and a fragment Fc (crystallizable fraction). The fragment Fc is the substrate of the immunoglobulins effector functions.

A fragment F(ab')2 is generated by pepsine digestion where both fragments Fab remain fixed by two disulfide bridges and the fragment Fc is split in several peptides. The fragment F(ab')2 is formed by two fragments Fab' (one fragment Fab' consisting of one Fab and of one hinge region), bound by intercatenary disulfide bridges in order to form a F(ab)2.

Such fragments, which contain the binding site of the antibody, may have lost certain properties of the whole antibody from which they derive, such as the capacity to activate the complement or to bind the Fcgamma receptors. However, these fragments did not loose the capacity of the whole antibody to neutralize the inhibitor antibody. Thus, the invention relates also to fragments F(ab')2, Fab', Fab, of the region CDR or any of the modified version of any one of these fragments or region, of the 30D1 antibody. Particularly, these fragments have retained the capacity of the whole antibody to neutralize the BOIIB2 antibodies.

A further subject matter of the invention is a stable cell line producing an antibody as previously described. The stable cell line of the invention can be of human or animal origin. The stable cell line of the invention can be derived from human immortalized cells. In a further embodiment of the invention, this cell line can be derived from immortalized animal cells, for example mice. A preferred example of a cell line derived from this embodiment of the invention is the line 30D1 deposited at CNCM under the accession number I-3450. In a further embodiment, the stable cell line of the invention is a cell line, which was integrated into a genetic construction enabling the expression of the antibody of the invention at the desired site of the genome. The step consisting in the obtaining of such a cell is a stable transfection. This step can be applied to any type of cells, provided they can be maintained in in vitro culture. The stable transfection requires the integration of the genetic construction, which can be made by homologous recombination or randomly. It is the presence of a positive selection box in the genetic construction comprising the gene of interest, which confers to the cell for example a resistance to antibiotics, which attests the insertion of the transgene into the cell genome. As result of a subcloning step, a long term antibody of the invention producer cell line is obtained, for example 30D1, which can be maintained in in vitro culture.

The stable cell line expressing an antibody of the invention can be selected from a group consisting of a human cell line, a rodent cell line, for example a mouse line, SP2/0, YB2/0, IR983F, a human myeloma such as Namalwa, or any other cell of human origin, like PERC6, the CHO lines, especially CHO-K-1, CHO-Lec10, CHO-Lec1, CHO-Lec13, CHO Pro-5, CHO dhfr- (CHO DX B11, CHO DG44), or further lines selected from Wil-2, Jurkat, Vero, Molt-4, COS-7, 293-HEK, BHK, K6H6, NSO, SP2/0-Ag 14 and P3X63Ag8.653.

A further particular subject matter of the invention is the 30D1 hybridoma deposited under the accession number CNCM I-3450 at the Collection Nationale de Cultures de Microorganismes (CNCM). The variable region of each of the light chains of the monoclonal anti-idiotypic antibody produced by the 30D1 hybridoma is encoded by the nucleic acid sequence SEQ ID NO: 2, and the variable region of each of the heavy chains of the monoclonal anti-idiotypic antibody produced by the 30D1 hybridoma is encoded by the nucleic acid sequence SEQ ID NO: 1. The antibody produced by the 30D1 hybridoma is the 30D1 antibody, and a method for obtaining the 30D1 hybridoma is described in the part <<Examples>> of the present document.

A further subject matter of the invention is a DNA fragment of sequence SEQ ID NO: 1 encoding the variable region of the heavy chain of the antibody of the invention as previously described. This DNA fragment can be inserted into a vector enabling the expression of a polypeptide, preferentially of an antibody, the variable region of the heavy chain of which is encoded by the nucleic acid sequence SED ID NO: 1, the derived peptide sequence of which is the sequence SEQ ID NO: 3, in order to be introduced into and maintained in a host cell. This vector enables the expression of this exogenous nucleic acid fragment in the host cell, because it contains the sequences (promoters, polyadenylation sequence, selection genes) essential to this expression.

Such vectors are well known to those skilled in the art and can be an adenovirus, a retrovirus, a plasmid or a bacteriophage, this list being not limiting. Further, any mammal cell can be used as host cell, that is as cell expressing the polypeptide or the antibody of the invention, for example SP2/0, YB2/0, IR983F, a human myeloma as Namalwa or any other cell of human origin like PERC6, the CHO lines, especially CHO-K-1, CHO-Lec10, CHO-Lec1, CHO-Lec13, CHO Pro-5, CHO dhfr- (CHO DX B11, CHO DG44), or other cell lines selected from Wil-2, Jurkat, Vero, Molt-4, COS-7, 293-HEK, BHK, K6H6, NSO, SP2/0-Ag 14 and P3X63Ag8.653.

A further subject matter of the invention is a DNA fragment of sequence SEQ ID NO: 2 encoding the variable region of the light chain of an antibody of the invention as previously described. This DNA fragment can be inserted in a vector allowing the expression of a polypeptide, preferably of an antibody, the variable region of the light chain of which is encoded by the nucleic acid sequence SED ID NO: 2, the derived peptide sequence of which is the sequence SEQ ID NO: 4, in order to be introduced into and maintained in the host cell. This vector allows the expression of this exogenous nucleic acid fragment in the host cell, because it contains the sequences (promoters, polyadenylation sequence, selection genes) essential to this expression. Such vectors are well known to those skilled in the art and can be an adenovirus, a retrovirus, a plasmid or a bacteriophage, this list being not limiting. Further, any mammal cell can be used as host cell, i.e. as cell expressing the polypeptide or the antibody of the invention, for example SP2/0, YB2/0, IR983F, a human myeloma as Namalwa or any other cell of human origin like PERC6, the CHO lines, especially CHO-K-1, CHO-Lec10, CHO-Lec1, CHO-Lec13, CHO Pro-5, CHO dhfr- (CHO DX B11, CHO DG44), or further cell lines selected from Wil-2, Jurkat, Vero, Molt-4, COS-7, 293-HEK, BHK, K6H6, NSO, SP2/0-Ag 14 and P3X63Ag8.653.

A further subject matter of the invention is a pharmaceutical composition comprising an antibody of the invention and at least an excipient and/or at least a pharmaceutically acceptable vehicle. Preferably, the monoclonal anti-idiotypic antibody contained in the pharmaceutical composition of the invention is the 30D1 antibody, a fragment or a region derived from 30D1, or a chimeric or humanized antibody comprising the variable regions of 30D1 and such as previously described in the present document. The pharmaceutical composition of the invention can be formulated in any excipient tolerated by a treated patient. Examples of such excipients include water, saline solutions, the Ringer solution, dextrose solutions, and any other suitable aqueous physiologic solution. The excipient can also contain low amounts of additives such as substances increasing the isotonicity and the stability of the composition. Such excipients include the phosphate buffer, the bicarbonate buffer and the Tris buffer. Such excipients are well known to those skilled in the art.

The standard formulations can be formulated as liquid for injections or as solid formulations which can be resuspended in a suitable liquid prior to administration. The vehicles which can be used for preparing of the pharmaceutical composition of the invention have advantageously the function of increasing the half-life of the therapeutic composition in the animal or the patient, or to enable the controlled delivery of the active principle. Such vehicles may be organic and synthetic polymers and other chemical compounds, which can disseminate the drugs at a normal rate or to disseminate in certain environments only, and liposomes as well, this list being not limiting.

Advantageously, the pharmaceutical composition of the invention comprises furthermore at least one anti-idiotypic antibody directed against an inhibitor antibody binding to a different domain than the domain A2 of Factor VIII. This further antibody can be an anti-idiotypic antibody directed against an inhibitor antibody binding to the domain A1, or A3, or B, C1 or C2 of Factor VIII. Indeed, a patient suffering from haemophilia A, having developed the inhibitor antibodies, most frequently exhibits several types of inhibitor antibodies. Moreover, the amounts and the nature of different types of inhibitor antibodies are not fixed, but may change in the course of life of the patient. The different inhibitor antibodies of one same patient being thus directed against the different domains of Factor VIII, it is particularly advantageous to treat the patient not with one, but with several types of anti-idiotypic antibodies, directed against different inhibitor antibodies.

Preferably, the pharmaceutical composition comprises a monoclonal anti-idiotypic antibody directed against an inhibitor antibody binding to the Factor VIII domain C2 and the monoclonal antibody of the invention. Indeed, the domains A2 and C2 are the main targets of the anti-Factor VIII immune reaction. Thus, a pharmaceutical composition comprising a mixture of anti-idiotypic antibodies directed against the inhibitor antibodies binding to the domain A2 of Factor VIII and of anti-idiotypic antibodies directed against the inhibitor antibodies binding to the domain C2 enables to neutralize at least 70%, and advantageously at least 80% or 90%, of all inhibitor antibodies present in a patient. In a preferred embodiment of the invention, the pharmaceutical composition of the invention comprises the 14C12 antibody (deposited under the accession number LMBP 5878CB at the Belgian Coordinated Collections of Microorganisms) and the 30D1 antibody. In a further preferred embodiment of the invention, the pharmaceutical composition comprises the 14C12 antibody and a chimeric or humanized antibody derived from the 30D1 antibody, i.e. an antibody comprising the variable regions of the 30D1 antibody.

A further subject matter of the invention is the use of the antibody of the invention as drug.

A further subject matter of the invention is the use of the antibody for the manufacturing of a drug. Advantageously, such a drug is used for reducing and/or preventing and/or treating bleedings in a patient suffering from haemophilia comprising the inhibitor antibodies directed against the domain A2 of Factor VIII.

A further subject matter of the invention is the use of the antibody of the invention for the manufacturing of a drug for the treatment of haemophilia type A.

Advantageously, haemophilia of type A treated in this way is a haemophilia with inhibitors. This type of haemophilia treated with the antibody of the invention can be innate or acquired. The antibody of the invention neutralizing the inhibitor antibodies, restores the efficiency of the treatment by injection of Factor VIII to the patient, the activity of Factor VIII being not inhibited anymore by inhibitor antibodies.

A further subject matter of the invention is the use of the antibody of the invention to neutralize in vitro or in vivo the inhibitor activity of an inhibitor antibody directed against the domain A2 of Factor VIII. This process can be carried out in order to deplete the blood of a patient of its inhibitor antibodies directed against the domain A2 of Factor VIII, the blood being afterwards re-injected to said patient.

A further subject matter of the invention is the use of the antibody for absorbing the inhibitor antibodies, for example for purifying the Factor VIII inhibitor antibodies.

Finally, a further subject matter of the invention is the use of the antibody of the invention to detect and/or to purify the Factor VIII inhibitor antibodies. The processes of such methods of detection and purification to be carried out are well known to those skilled in the art. For example, the use to this end of an immunopurification column containing beads, the surface of which is grafted with the antibody of the invention. Only the molecules recognized by the antibody will bind to the beads. The others will pass through the column. For recovering of the molecule, an increase of the ionic strength of the solvent is sufficient.

Further aspects and advantages of the invention will be described in the following Examples, which are intended to depict the invention and not to limit its scope.

DESCRIPTION OF THE FIGURES

FIG. 8: The addition of 30D1 allows to efficiently neutralize, in vivo, the inhibitor activity activity of the anti-FVII BOIIB2 antibody.

EXAMPLES

Example 1

Production of a Human Monoclonal Antibody Directed Against the Domain A2 of Factor VIII
(<<Anti-A2 Antibody>>)

Human monoclonal antibodies, having the desired specificity and the characteristics, are produced by transformation of B lymphocytes obtained from peripheral blood of individuals, preferably patients suffering from haemophilia A or acquired heamophilia. B cells are transformed by infection with the Epstein-Barr virus and by surface antigen activation, thanks to techniques well known to those skilled in the art (Madec et al. (1996) J Immunol 156:3541-3549). The cell supernatants containing the desired antibody are identified by specific tests.

Thus, the antibodies directed to Factor VIII are identified by reacting the supernatant with polystyrene plates coated with Factor VIII or with a complex Factor VIII/von Willebrand Factor. The binding of specific antibodies is detected by addition of an anti-human IgG coupled with an enzyme. The addition of an enzyme substrate converted in a colored compound in presence of an enzyme allows to detect specific antibodies. Such methods referred to as ELISA (Enzyme-Linked Immuno-Sorbent Assays), are well known to those skilled in the art. A detailed description is available in <<Current Protocols in Immunology, Chapter 2, John Wiley & Sons, Inc, 1994>>.

The B cells producing the anti-Factor VIII antibodies are later expanded and cloned by limit dilutions. Methods of cloning are described, for example, in <<Current Protocols in Immunology, Chapter 2, John Wiley & Sons, Inc. 1994>>.

Figure 1:
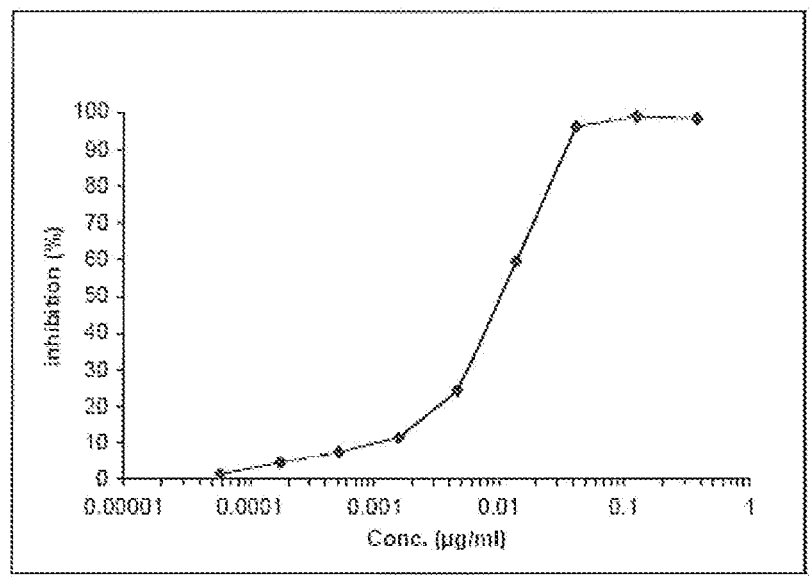
FIG. 1: Evaluation of the antibody BOIIB2 capacity to inhibit the Factor VIII in a functional assay

The anti-Factor VIII antibodies exhibiting the desired characteristics, namely the capacity to inhibit the procoagulant activity of Factor VIII, are identified by use of commercially available chromogenic test kits, following the instructions of the manufacturer. Antibodies which inhibit the functionality of Factor VIII and exhibit a sufficient affinity to bind the Factor VIII, are selected. The FIG. 1 shows the property of an antibody, referred to as BOIIB2, specific of the domain A2 of Factor VIII, to inhibit the Factor VIII in a functional assay. The used functional assay is a chromogenic assay in which the Factor VIII activated by thrombin acts as a cofactor to Factor IXa in the conversion of Factor X in Factor Xa. Briefly, 20 µl of recombinant Factor VIII (recFVIII) diluted in a solution of PBS-BSA (1 IU/ml) are mixed with an equal volume of a serial dilution of the BOIIB2 antibody in the same solution of PBS-BSA and incubated for 1 hour at 37° C. 20 µl of the mixture are then incubated for 3 minutes at room temperature in a microtiter well with 20 µl of reagent 1 (Factor X) and 20 µl of reagent 2 (Factor IXa) prior to addition of 100 µl of reagent 3 (chromogenic substrate and blocking buffer). Control experiments including the recFVIII incubated without specific antibodies or with the same concentration of irrelevant antibodies are carried out. The coloration density of the substrate is directly measured at 405 nm with a reference at 450 nm. The percentage of inhibition is calculated by comparison to the positive control recFVIII 1 IU/ml. The curve indicates that the BOIIB2 inhibits the FVIII to 99% in a concentration of 0.1 µg/ml.

Alternatively, antibodies having the required characteristics can be produced by immunization of animals. In this case, the human Factor VIII is injected to mice with an adjuvant. The anti-human monoclonal antibodies are then obtained by fusion of spleen lymphocytes with a mouse myeloma cell line. The cellular supernatants producing the anti-Factor VIII antibodies are identified and cloned by limit dilution. A general description of such methods can be found in <<Current Protocols in Immunology, Chapter 2, John Wiley & Sons, Inc. 1994>>. Further selections of inhibitors exhibiting the desired characteristics are described here-above.

Antibodies produced in mice are humanized. Thus the sequences of the variable murine parts of the heavy and light chains are aligned with the variable regions of human immunoglobulin in a way to identify a human antibody having the best homology of the framework regions (FR). The DNA fragment encoding the humanized variable regions is then synthetized by the PCR-based CDR grafted method, described in Sato K et al. (1993); Cancer Research 53: 851-856.

Example 2

Characterization of the Specificity and of the Affinity of Anti-A2 Antibodies

The specificity of antibodies directed against the domain A2 of Factor VIII is characterized by means of a combined transcription-translation system with rabbit reticulocytes. To this end, a plasmid bank containing different fragments of the domain A2, is constructed.

The plasmid construction pSP64—FVIII (ATCC, Rockville, Md.) containing a complete cDNA of 7.2 kb is used as template to generate all the fragments by PCR. The fragments of cDNA carrying mutations or deletions are produced by DOE-PCR (Splicing by Overlap Extension-PCR). A tag sequence, including the ubiquitin and/or epitope tag T7 for the specific recognition of the anti-tag antibodies, is added to Factor VIII fragments of less of 15 amino acids, as well as a complementary sequence of cysteins for labeling. The polypeptide fragments of Factor VIII are produced by the method of "TNT COUPLED RETICULOCYTE LYSATE SYSTEMS" (Promega), following instructions of the manufacturer.

The immunoprecipitation of the transcribed genes is carried out as follows. Sample dilutions containing the specific antibodies are mixed with 40 µl PROTEIN A SEPHAROSE (Pharmacia) in 500 µl of a suitable buffer, and the mixture is gently stirred for 1 hour at 4° C. The non-fixed antibodies are eliminated by means of a succession of centrifugations and washings. The complex antibody PROTEIN A SEPHAROSE is resuspended in 300 µl of buffer supplemented with 3 µl of polypeptides of Factor VIII labeled in vitro with methionin L-($^{35}$S), in order to incubate at 4° C. for 2 hours. The complexes antigens/antibodies are eluted from the beads by boiling for 3 minutes in 30 µl of denaturating buffer and the radioactivity is counted. A second aliquot is analyzed by SDS-PAGE and visualized by autoradiography.

Figure 2:
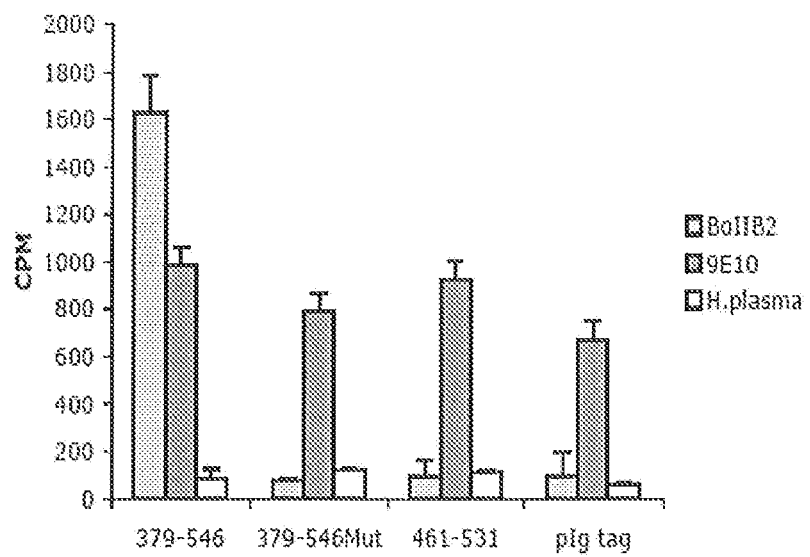
FIG. 2: Epitope mapping of the BOIIB2 antibody.
Figure 3:
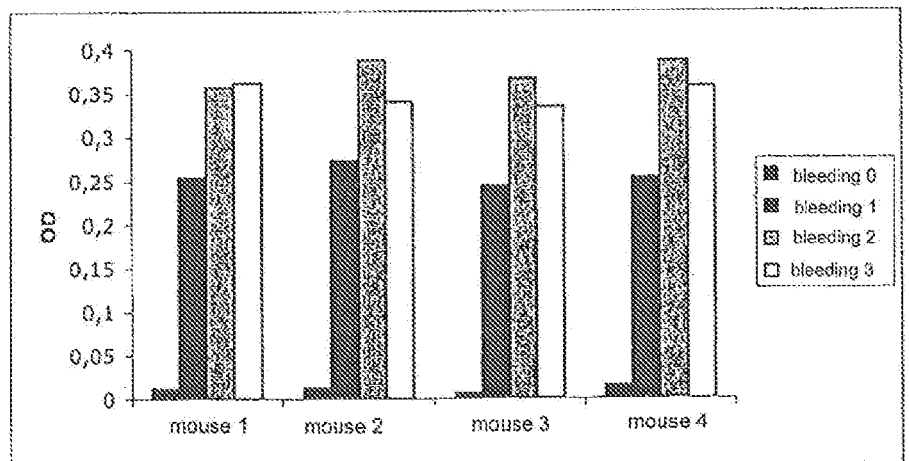
FIG. 3: Bleeding dependent immune response of mice injected with the BOIIB2 antibody by measurement of the optical density.
Figure 4:
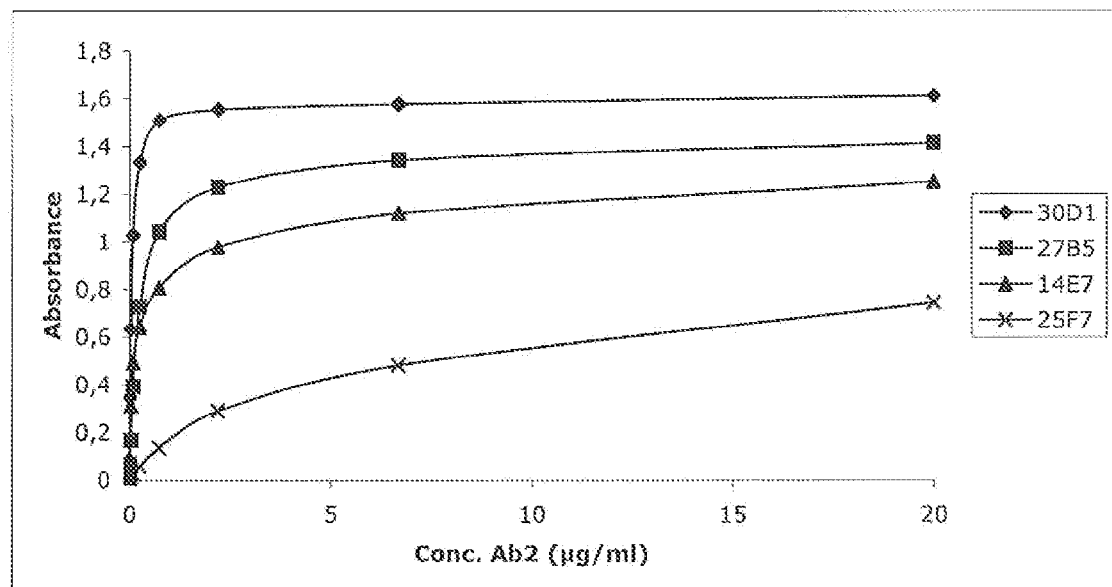
FIG. 4: Direct binding of the anti-idiotypic antibodies to insolubilized BOIIB2 antibody.
Figure 5:
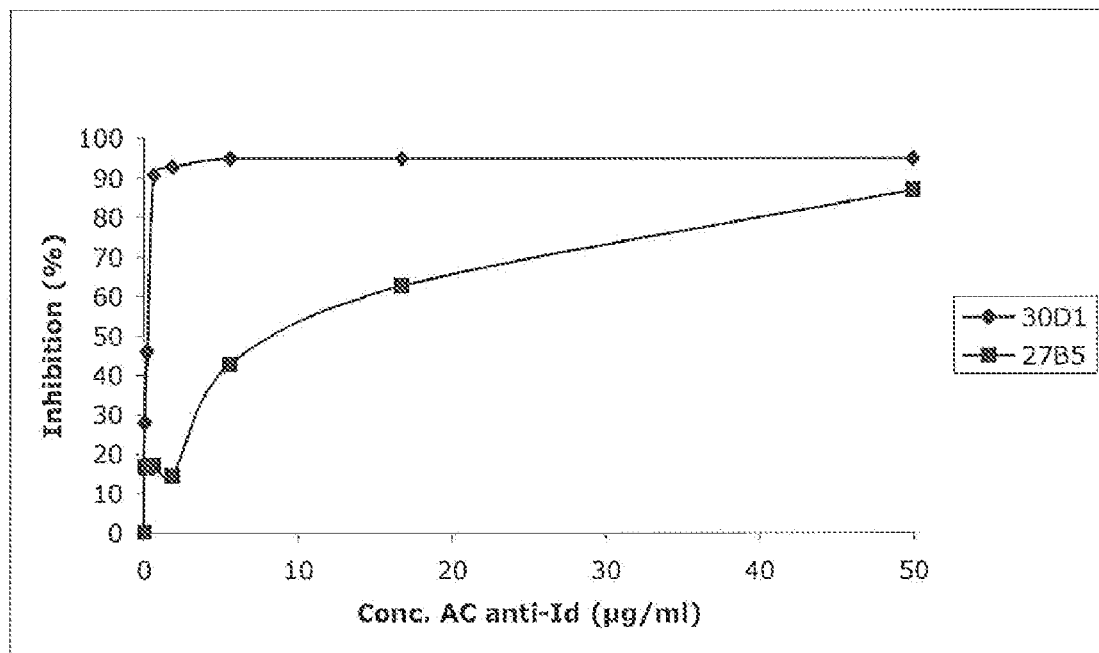
FIG. 5: Inhibition of the binding of the antibody BOIIB2 to recombinant insolubilized Factor VIII

The FIG. 2 shows the results of such an experience for the BOIIB2 antibody. The residues carrying the sequence tag of the regions 379-546, 379-546Mut (R484A, Y487A, R489A, P492A) and 461-531, were labeled and produced by the lysates of reticulocytes. The fragments were immunoprecipitated by the human BOIIB2 antibody bound to Protein-A Sepharose. After washing, the complex was eluted and the radioactivity measured (in CPM) by scintillation and charged on SDS-PAGE, followed by an autoradiography. The binding of the BOIIB2 to the domain A2 including the residues 379-546 is shown. In any case, the binding was abolished when 4 mutations were introduced into the region or when the region was truncated of its N-terminal part (461-531). The anti-c-myc 9E10 antibody and the human plasma were used as positive and negative controls, respectively.

A binding site in the region comprising the residues 389-510 is identified within the domain A2. However, a more precise layout of the epitope is difficult because the removal of amino-terminal or carboxy-terminal parts of such fragments abolishes rapidly the binding of the antibody. The Applicants have therefore used a stepwise approach to introduce unique mutations into the presumed binding site, namely 484-509. The FIG. 2 shows that the unique mutations in such a site abolish the binding of the antibody. Moreover, the unique mutations were introduced in the sequence of 3 glutamic acids located within 389-391, also resulting in a loss of binding. Thus, it is possible to conclude that the binding site is located within the amino acids 484-509, but that the 3 glutamic acid residues are required at a certain distance for an efficient binding of the antibody.

The affinity of the antibody is calculated by means of a system <<Surface Plasmon Resonance>>. By this means, the kinetics of interaction between the Factor VIII and the human antibody in real time is analyzed by means of an instrument by Pharmacia BIOSENSOR BIACORE™ (Pharmacia Biosensore AB). The purified BOIIB2 antibody (20 μg/ml in sodium acetate buffer 10 mM pH 5.0) is immobilized on an activated surface of a chip <<CME sensor chip>>, following the instruction of the manufacturer. All experiments were carried out in HBS, at a constant flow of 10 μl/min. The Factor VIII in HBS is infused in different concentrations through the ECRs immobilized on a surface probe. At the end of each cycle, the surface is regenerated by rinsing with HCl, pH 2, for 36 sec. The association and dissociation constants are determined by means of an assessment computer program BIA using models assuming the binding of an analyte to one or two immobilized ligands.

The $k_{diss}$ of BOIIB2 was assessed to $1.10^{-8}$ $s^{-1}$ and the $k_{ass}$ of BOIIB2 was assessed to $1.10^{3}$ $M^{-1}$ $s^{-1}$.

Example 3

Sequencing of the BOIIB2 Antibody

The RNA isolation from human B cell lines immortalized by EBV is performed using the reagent TRIZOL following the instructions of the manufacturer (Life Technologies). The cDNA is synthetized by the Superscript pre-amplification system for the synthesis of the first strand of cDNA. The cDNA encoding the variable region of the heavy chain (VH) of the antibody is amplified by PCR with specific primers of the leader sequence of families VH and for the first exon of the region CH, as described by Jacquemin et al. (2000); Blood. January 1; 95(1):156-63. The pairing is carried out at 60° C. in 40 cycles of PCR. The PCR products of suitable size (460 bp) are isolated from agarose gel of 1.5% and cloned by use of the kit TA CLONING (Invitogen BV, Leek, The Netherlands). A PCR screening by means of couples of primers corresponding to the family of the gene VH of interest is carried out on randomized colony cultures. The plasmid DNA of the positive colonies is isolated by means of WIZARD PLUS MINIPREPS (Promega, Menio Park, Cailf.) and sequenced in the two directions with SEQUENASE (United States Biochemical, Cleveland, Ohio), following the instructions of the manufacturer. The sequence analysis of the variable region gene is carried out by means of <<V BASE Sequence Directory>> (Tomlinson et al., MRC Centre for protein Engineering, Cambridge, UK).

The VH gene of BOIIB2 belongs to the group H4 and is a homologous to DP-71. The segment J is homologous to JH6c. The gene sequencing of the cloned light chain identified the VL as a VLIII and the segment J as a JL5.

The nucleotide sequence of the heavy chain of BOIIB2 is the sequence SEQ ID NO: 5, and the nucleotide sequence of the light chain of the antibody BOIIB2 is the sequence SEQ ID NO: 6. The peptide sequence corresponding to the sequence SEQ ID NO: 5 is the sequence SEQ ID NO: 7 and the peptide sequence corresponding to the sequence SEQ ID NO: 6 is the sequence SEQ ID NO: 8.

Example 4

Production of the Anti-Idiotypic Antibody 30D1

I. Mice Immunization

Four Balb/c female mice, 6-weeks old, received a subcutaneous (SC) injection in the foot-pad, three times, of 10 ng of the FVIII anti-domain A2 BOIIB2 human antibody suspended in Freund's complete adjuvant (FCA) (first immunization) then in the Freund's incomplete adjuvant (FIA).

A first bleeding (bleeding 0) was performed before the immunization (bleeding on J0), then the injections and bleedings followed as set forth hereafter:

J1: Injection n°1 (10 μg of BOIIB2 antibody in presence of Freund's complete adjuvant)
J15: Bleeding n°1
J16: Injection n°2 (10 μg of BOIIB2 antibody in presence of Freund's incomplete adjuvant)
J28: Bleeding n°2
J29: Injection n°3 (10 μg of BOIIB2 antibody in presence of Freund's incomplete adjuvant)
J44: Bleeding n°3

II. Evaluation of the Immune Response in Mice

In order to evaluate the presence of anti-BOIIB2 antibodies in the different bleedings, an ELISA test in direct fixation is performed. To this end, the BOIIB2 antibody in 3 μg/ml, 50 μl/well, in glycin buffer, ON (over night) at 4°C. (glycin buffer=glycin 0.1M, NaCl 0.17M, pH 9.2) is insolubilized. Three washings with PBS/Tween are performed (PBS=NaCl 140.0 mM, KCl 2.6 mM, $KH_2PO_4$ 1.4 mM, $Na_2HPO_4.2H_2O$ 8.1 nM, pH 7.4). The system is left to saturation for 30 minutes at room temperature (RT) with 100 μl/well of Magic Buffer (Magic Buffer=Tris 50 mM, NaCl 0.17M, BSA 1%, pH 7.2). The bleedings are then diluted to 1/10, 1/50, 1/250 and 1/1250 in the Magic Buffer and incubated for 2 hours at room temperature (RT) (50 μl/well). Then 3 washings were performed with PBS/Tween. Then the system is incubated with a solution of goat polyclonal mouse anti-IgG antibodies labeled with HRP (horseradish peroxidase) (Bio-Rad) to 1 μg/ml for 2 hours at room temperature (RT) (50 μl/well) (dilution in the Magic Buffer). Afterwards, the system is washed 3 times with PBS/Tween, then revealed with a chromogen (Orthophenyl diamine) and the obtained coloration intensity was read with a reader with filters corresponding to wavelengths 490/650 nm (reader Emax Molecular Devices, Sunnyvale, Calif.).

Results obtained for the optical density:

| Dilution 250X | Mouse 1 | Mouse 2 | Mouse 3 | Mouse 4 |
|---|---|---|---|---|
| Bleeding 0 | 0.012 | 0.013 | 0.006 | 0.016 |
| Bleeding 1 | 0.255 | 0.273 | 0.245 | 0.254 |
| Bleeding 2 | 0.357 | 0.388 | 0.366 | 0.386 |
| Bleeding 3 | 0.362 | 0.34 | 0.334 | 0.357 |

The obtained results are reported on the FIG. 7.

Conclusion: each mouse exhibited a correct response and in a similar way to the BOIIB2 antibody injection. In a arbitrary way, the mouse n °2 was selected to perform the fusion.

III. Fusion and Screening

Spleen lymphocytes of the mouse n °2 were fused with myeloma cells SP2/0. The fusion was performed in a classical way known to those skilled in the art (J. G. Gilles et al. Blood (2004) 103 : 2617-23; P. Cornelis, <<Les anticorps monoclonaux>>, Revue IRE, vol. 7, n °4, 1983).

The cells were expanded successively in a DMEM medium (Dulbecco's Modified Eagle Medium) containing hypoxanthin and thymidin following the principle of limit dilutions and the clones tested positive detected by a test of direct fixation ELISA such as previously described under point II.

The specificity of the fixation was confirmed with a human antibody IgG4 of non relevant specificity anti-Der P2 (AK6A3, antibody directed against one of the major allergens of the acarid *Dermatophagoides Pteronisinus* (DPT)) available in the Applicant's laboratory. It is evident for those skilled in the art that any other antibody of a different isotype than IgG4 can be used as negative control.

In order to determine the stability of the hybridomas, the Applicants repeated the assay (assays 1 a 3) upon the expansion of the clones, in different volumes of medium ranging from 200 µl to 5 ml.
Assay 1=measurement in well of 200 µl
Assay 2=measurement in well of 1 ml
Assay 3=measurement in bottle of 5 ml
Results of optical density:

|  | Assay 1 | | Assay 2 | | Assay 3 | |
| --- | --- | --- | --- | --- | --- | --- |
| clone | BOIIB2 | IgG4 (AK6A3) | BOIIB2 | IgG4 (AK6A3) | BOIIB2 | IgG4 (AK6A3) |
| 10C11 | 0.353 | 0.094 | dead clone | dead clone | dead clone | dead clone |
| 10H7 | 0.436 | 0.093 | dead clone | dead clone | dead clone | dead clone |
| 11F5 | 0.134 | 0.040 | dead clone | dead clone | dead clone | dead clone |
| 12F5 | 0.291 | 0.087 | 0.024 | 0.002 | 0.012 | 0.002 |
| 14E7 | 0.231 | 0.077 | 0.234 | 0.006 | 0.216 | 0.003 |
| 25F7 | 0.362 | 0.071 | 0.205 | 0.003 | 0.178 | 0.002 |
| 27B5 | 0.333 | 0.046 | 0.238 | 0.003 | 0.259 | 0.003 |
| 28C5 | 0.125 | 0.077 | dead clone | dead clone | dead clone | dead clone |
| 30D1 | 0.324 | 0.093 | 0.311 | 0.003 | 0.293 | 0.002 |

Conclusion: 4 clones are positive in direct fixation to the antibody BOIIB2: 14E7, 25F7, 27B5, 30D1. These clones are stable in the three assays.

IV. Inhibition Assay with Culture Supernatants

In order to select an anti-idiotypic antibodies (Ac anti-Id) producer clone, which recognizes precisely an epitope determinant located at the level of the paratope of the antibody BOIIB2 among the 4 clones retained in the point III, the anti-Id antibodies were assayed in an ELISA assay of inhibition of the BOIIB2 binding to insolubilized FVIII. The recombinant Factor VIII (recFVIII) (Baxter) at 2 µg/ml in a glycin buffer, 50 µl/well, was insolubilized, then left for 2 hours at room temperature. The BOIIB2 antibody (or an irrelevant IgG4) in final amount of 0.4 µg/ml was incubated for 2 hours with the supernatants of antibodies culture 14E7, 25F7, 27B5, 30D1 in a dilution of 1/1, 1/2 and 1/4 in the Magic Buffer. The wells were washed 3 times with a PBS/Tween buffer, then a saturation with 100 µl/well of Magic Buffer (30 min at room temperature) is performed. Afterwards, an incubation with 50 µl of BOIIB2 (or irrelevant IgG4) and the culture supernatant (2H, RT, Magic Buffer), then three washings were performed. The BOIIB2 antibodies fixed to insolubilized recFVIII are detected by adding 50 µl/well of a solution of 1 µg/ml in the Magic Buffer of mouse polyclonal human anti-IgG HPR-labelled (Southern Biotechnology). Three successive washings were performed with PBS/Tween, later the revealing was carried out with a chromogen (OPD ortho-phenyl diamine) and reading of the intensity of the obtained coloration by means of a reader with filters corresponding to wavelengths of 490/650 nm (reader Emax Molecular Devices, Sunnyvale, Calif.).

The inhibition is calculated as follows:

$$I(\%)=1-(\text{signal with anti-idiotypic antibody/signal without anti-idiotypic antibody})$$

Obtained results:

| Clones | Inihibition (%), dilution 1/1 |
| --- | --- |
| 14E7 | 0 |
| 30D1 | 73 |
| 27B5 | 0 |
| 25F7 | 0 |

Conclusions: only one clone (30DA1) is able to specifically inhibit the fixation of the antibody BOIIB2 to insolubilized recFVIII V. Production of 4 Producer Clones of Anti-BOIIB2 Antibodies in an Extensive Manner In order to have available larger amounts of antibodies allowing to confirm the specificity of the antibodies 14E7, 25F7, 27B5, 30D1 from Example IV, the Applicants produced these anti-idiotypic antibodies in culture medium DMEM followed by purification on a Protein G affinity column which allows to purify, then concentrate the antibodies and to more ascertain the specificity of the obtained anti-idiotypic antibodies.

Figure 6:
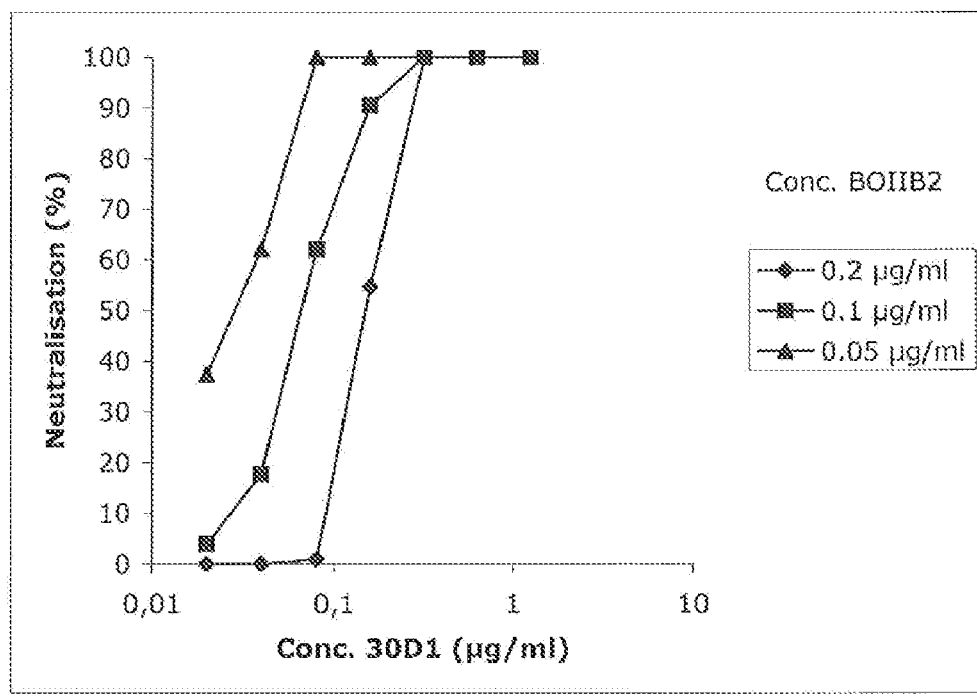
FIG. 6: Neutralization of the BOIIB2 antibody anti-Factor VIII inhibitor activity.

The concentration of the purified antibodies was measured by photometry, in a classical way known to those skilled in the art.
30D1: production of 4 ml at 3.23 mg/ml
27B5: production of 7.5 ml at 3.24 mg/ml
14E7: production of 4 ml at. 2.74 mg/ml
25F7: production of 5 ml at 0.392 mg/ml
The obtained amounts of the different antibodies are:
30D1: 12.92 mg
27B5: 24.3 mg
14E7: 10.96 mg
25F7: 1.96 mg VI. Specificity Evaluation The different preparations are assessed by an ELISA following the same protocol as that described in points II and IV.
6.1 ELISA Assay: direct binding of anti-idiotypic antibodies 14E7, 25F7, 27B5, 30D1 to the insolubilized BOIIB2 antibodies The results are shown in FIG. 6. The four antibodies bind in a dose-dependent manner to the insolubilized BOIIB2 antibody on plate. The results suggest an affinity that is different of the four antibodies, which decreases in the following order: 30D1, 27B5, 14E7, 25F7.
6.2. ELISA Assay: Inhibition of the Antibody BOIIB2 Fixation to the Insolubilized recFVIII The used protocol is the same as the protocol described under point IV.

The used BOIIB2 concentration is equal to 0.4 µg/ml, which is the concentration capable to inhibit of about 90% of the activity of one unit of FVIII.

The inhibition is calculated as follows:

$$I(\%)=1-(\text{signal with anti-idiotypic antibody/signal without anti-idiotypic antibody})$$

| | Percentage of inhibition | | | |
|---|---|---|---|---|
| Conc. µg/ml | 30D1 | 27B5 | 14E7 | 25F7 |
| 50 | 94.8 | 86.9 | 0 | 0 |
| 16.7 | 94.8 | 62.7 | 0 | 0 |
| 5.56 | 94.8 | 42.8 | 0 | 0 |
| 1.85 | 92.7 | 14.4 | 0 | 0 |
| 0.62 | 90.6 | 17.1 | 0 | 0 |
| 0.21 | 46 | 16.5 | 0 | 0 |
| 0.07 | 28 | 16.7 | 0 | 0 |
| 0.023 | 17.5 | 16.8 | 0 | 0 |
| 0.0076 | 0 | 0 | 0 | 0 |
| 0.0025 | 0 | 0 | 0 | 0 |

Figure 7:
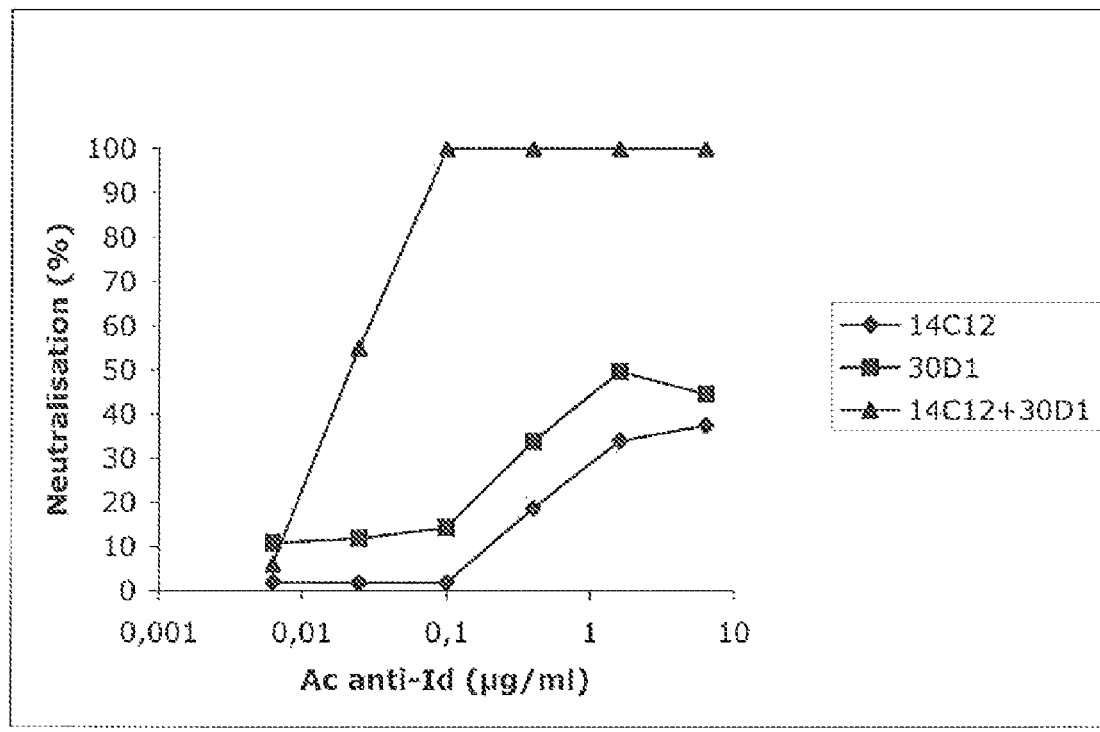
FIG. 7: Neutralization of the mixture of the BO2C11 antibody and the BOIIB2 antibody inhibitor effect with 14C12 and 30D1 anti-idiotypic antibodies.

The results are shown in FIG. 7. The 30D1 and 27B5 antibodies exhibit an inhibitor effect, whereas the 14E7 and 25F7 antibodies are negative. The inhibitor effects of the 30D1 and 27B5 antibodies are distinguished quantitatively. Whereas 30D1 gives raise to an inhibition with very low doses (90% inhibition at 0.6 µg/ml and a maximum of 94.8% at less than 6 µg/ml), it is necessary to use about 10 µg/ml to reach an inhibition of 50%.

6.3. Functional Assay: Measurement of the Neutralization of the BOIIB2 Antibody Inhibitor Activity (Anti-FVIII). Depending on the Results Obtained in the Previous Example, Only the 30D1 Antibody is evaluated.

The BOIIB2 antibody is incubated in different concentrations (of 1.6 to 0.05 µg/ml) with 30D1 anti-Id (dilution curve of 1.25 to final 0.02 µg/ml) in the Magic Buffer. After 30 min, the FVIII KOGENATE® (Bayer) in a final amount of 0.5 U/ml is added, then a complementary incubation for 30 min at 37° C. is carried out. The samples are diluted 30× in the Magic Buffer, then the reagents of the DADE chromogenic assay are added (chromogenic Factor VIII, Dade Behring Gmbh, Marburg, Germany) following the instructions of the manufacturer.
Results:

| BOIIB2 (µg/ml) | 0.2 µg/ml | 0.1 µg/ml | 0.05 µg/ml |
|---|---|---|---|
| 30D1 (µg/ml) | | | |
| 1.25 | 100 | 100 | 100 |
| 0.63 | 100 | 100 | 100 |
| 0.32 | 100 | 100 | 100 |
| 0.16 | 54.6 | 90.5 | 100 |
| 0.08 | 0.9 | 61.9 | 100 |
| 0.04 | 0 | 17.6 | 62 |
| 0.02 | 0 | 3.9 | 37.3 |

The results are reproduced in FIG. 6. The results show that the 30D1 antibody neutralizes the BOIIB2 inhibitor activity in a dose-dependant manner.
The inhibition is calculated as follows:

$$I(\%) = 1 - (\text{signal with anti-idiotypic antibody/without anti-idiotypic antibody})$$

6.4. Measurement of the Kinetics of Fixation of the 30D1 Antibody Anti-Id by the Method "Surface Plasmon Resonance BIACORE"

The kinetics of fixation of the 30D1 anti-idiotypic antibody to the BOIIB2 inhibitor antibody was assessed by the method "Surface plasmon resonance BIACORE" using the Pharmacia BIOSENSOR BIACORE (Pharmacia Biosensor AB, Uppsala, Sweden). The BOIIB2 antibodies were immobilized on an activated surface of a probe CM5. The 30D1 anti-idiotypic antibodies were infused in several concentrations of immobilized BOIIB2 on the surface of the probe. The association and dissociation constants were determined:

$K_a(M-1S-1) = 6 \cdot 10^4$ $K_d(S-1) = 1 \cdot 10^{-5}$ $K_D: 1 \cdot 10^{-5} / 6 \cdot 10^4 = 0.17 \cdot 10^{-9}$ M.

6.5 Characterization of the 30D1 Antibody Sub-class

In order to determine the sub-class of the 30D1 Ab, the system ISOSTRIP from Roche was used (colorimetric strip). The 30D1 antibody is a IgG1, Kappa.

6.6 Sequence

For sequencing, the RNAm from hybridomas producing the 30D1 anti-idiotypic antibody was isolated using the QUICK PREP MICRO mRNA PURIFICATION KIT (Amersham Pharmacia Biotech, Uppsala, Sweden). The cDNA was synthesized using the FIRST-STRAND cDNA SYNTHESIS KIT (Amersham Pharmacia Biotech). cDNAs encoding the heavy chain (VH) and the light chain (VL) were amplified by PCR (Polymerase Chain Reaction) with specific primers corresponding to different gene families potentially occurring in mice. The PCR products were isolated from an agarose gel 1.5% using the QIA QUICK GEL EXTRACTION KIT (Qiagen, Hilden, Germany) and cloned using the pGEM-T EASY VECTOR SYSTEM (Promega, Madison, Wis.). The plasmid DNA of positive colonies was isolated with the HIGH PURE PLASMID ISOLATION KIT (Roche Diagnostics, Mannheim, Germany) and sequenced in both directions with SEQUENASE (US Biochemicals, Cleveland, Ohio).

Example 5

Neutralization of the Inhibitor Effect of the Mixture of BO2C11 Antibody and of BOIIB2 Antibody by 14C12 and 30D1 Anti-Idiotypic Antibodies A Bethesda assay was performed with the B02C11 and BOIIB2 monoclonal antibodies in order to assess the capacity of the 30D1 and 14C12 anti-idiotypic antibodies (antibody directed against an inhibitor antibody binding to the domain C2 of Factor VIII, described in the patent WO 2004/014955) to neutralize the inhibitor capacity of human anti-FVIII antibodies. The concentration of the BO2C11 (0.03 µg/ml)+ BOIIB2 (0.013 µg/ml) antibodies is defined as the concentration inhibiting 80% of the Factor VIII activity in the Bethesda assay.

The neutralization effect is assessed:

1° for each anti-idiotypic antibody added separately (14C12 --♦-- and BODI --■--) in a growing concentration (of 0.0063 to 6.4 µg/ml) to the mixture BO2C11+BOIIB2.

2° for the association of the 2 anti-idiotypic antibodies 14C12 and 30D1 (--▲--) added in same concentrations to the mixture BO2C11+BOIIB2.

The FIG. 7 shows that a combination of 2 anti-idiotypic antibodies targeting the inhibitor antibodies directed against the different domains of FVIII (domains A2 and C2) has a higher effect then anti-idiotypic antibody used alone.

Example 6

In vivo Neutralization of BOIIB2 Antibody (BOIIB2) Inhibitory Effect by the Anti-Idiotypic Antibody 30D1 (30D1) Assay 1) The BOIIB2 was pre-incubated in amounts of 2.5 µg/ml with different concentrations of 30D1 (200 µg/ml-20 µg/mg and 3 µg/ml) for 30 minutes at 37° C.

Intravenous injections (100 μl/mouse) were carried out:
either with the mixture BOIIB2/30D1
or with the mixture BOIIB2/IgG1
or with the BOIIB2 alone
or with physiologic serum
Each group comprised 6 mice.
2) Each mouse received an injection of 2 IU of FVIII (KOGE-NATE®) after 30 minutes.
3) The plasma from mice is collected after 30 minutes, in order to assess in vivo the neutralization of the inhibitory effect of BOIIB2 by the 30D1.
4) A chromogenic test is carried out.

| Activity ng/mn | FVIII | FVIII + BOIIB2 | 30D1 10 μg/ml | 30D1 1 μg/ml | 30D1 0.15 μg/ml | Ig1 CTI |
|---|---|---|---|---|---|---|
| Mean value | 219.8 | 5.0 | 244.6 | 208.5 | 5.0 | 3.8 |
| SEM | 7.1 | 1.1 | 1.2 | 31.7 | 1.9 | 0.7 |

Figure 8:
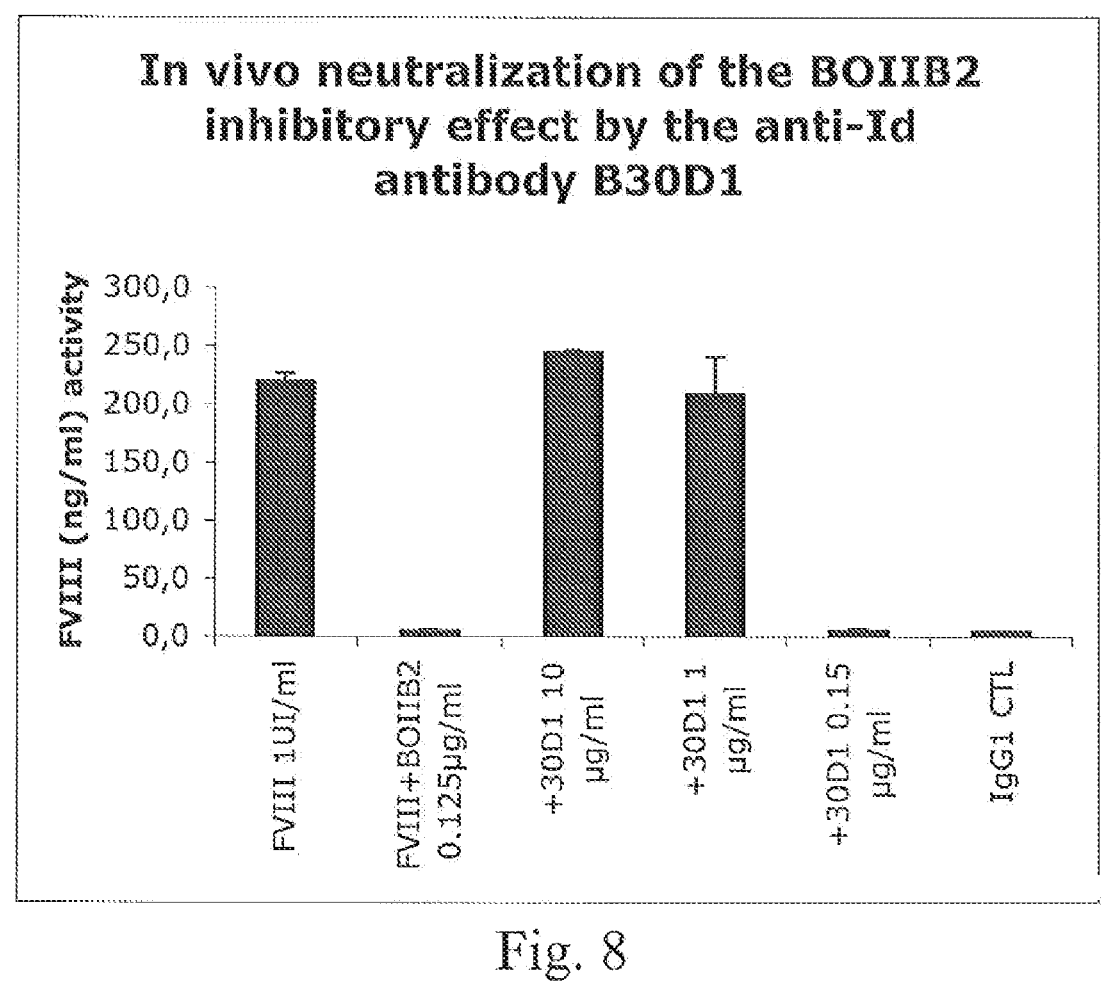

The results (FIG. 8) show that the addition of 30D1 allows to efficiently neutralize, in vivo, the inhibitor activity of the anti-FVII BOIIB2 antibody.

Example 7

Thrombin Generation in a Platelet-Rich Plasma in the Presence of the BOIIB2-30D1 Antibodies Mixture Citrated blood is subjected two times to a centrifugation at 900 rpm for 15 minutes in order to obtain a platelet-rich plasma (300 000 platelets/μl plasma). 80 μl of this platelet-rich plasma (PRP) is incubated for 5 minutes at 37° C. with 20 μl of HEPES 20 mM, NaCl 140 mM, BSA (Bovine Serum Albumin) 5 mg/ml, pH 7.35 buffer, containing the anti-FVIII BOIIB2 antibody at a ratio of 3 μg/ml, the anti-idiotypic antibody 30D1 in various concentrations from 3.75 μg/ml to 30 g/ml and the SINTACYL® beads (Instrumentation Laboratory-Orengburg-NY-USA) in a final dilution of 1/200 in a 96 wells plate. The SINTACYL® beads are negatively charged and induce the intrinsic pathway activation of the coagulation.

Fluo-buffer (Hepes 20 mM, BSA 60 mg/ml, pH 7.35 buffer) and $CaCl_2$ 1M are added to the fluorogenic substrate (Z-Gly-Gly-Arg-AMC) diluted to 100 mM with DMSO (dimethyl sulfoxide). 20 μl of this revealing solution (FluCa) solution) are added to each well and a few minutes later, the plate is read at well-lengths of 390/460 in a Thrombinoscope.

Figure 9:
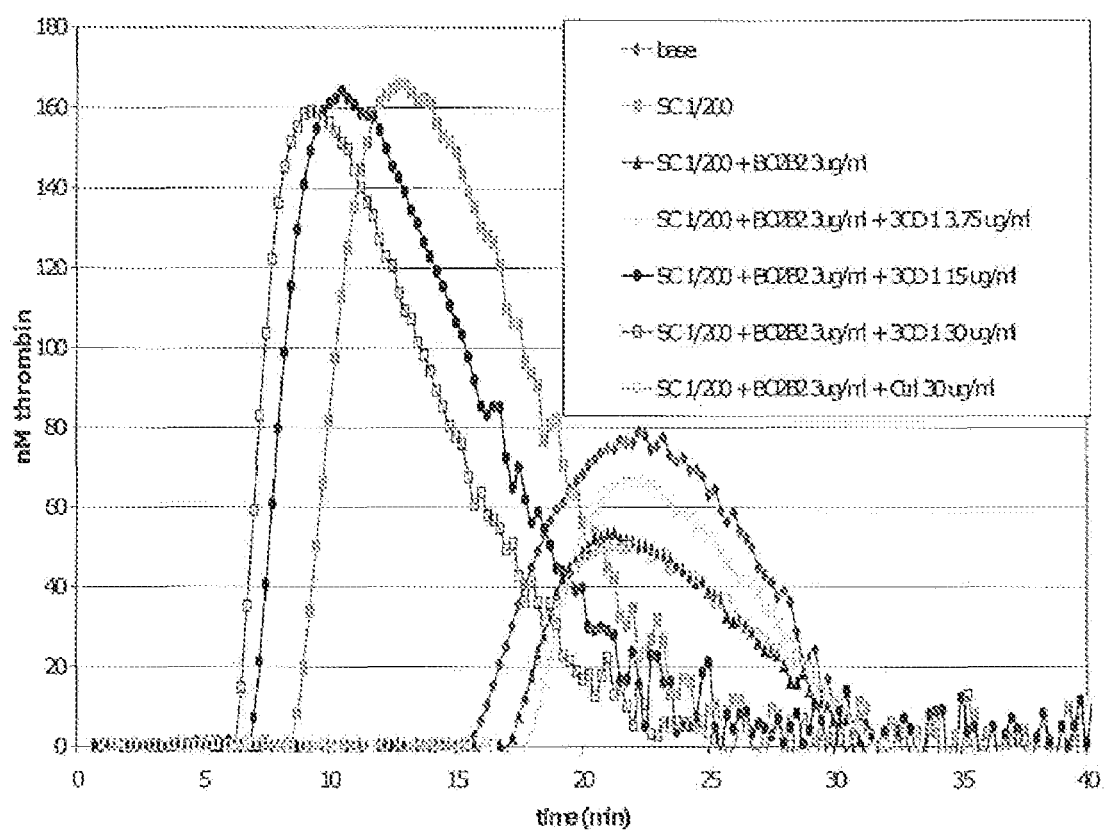
FIG. 9: Thrombin generation in the presence of presence of the anti-idiotypic antibody 30D1.

The obtained results (FIG. 9) show that, even in the presence of the inhibitory antibody BOIIB2, thrombin generation is allowed in the presence of the anti-idiotypic antibody 30D1.

The invention claimed is:

1. An isolated monoclonal anti-idiotypic antibody directed against a Factor VIII human inhibitor antibody, wherein said inhibitor antibody is directed against the A2 domain of human Factor VIII and recognizes an epitope located between amino acids 484 to 508 of human Factor VIII, wherein said inhibitor antibody is antibody BOIIB2 antibody (deposited to the Belgian Coordinated Collections of Microorganisms, under the accession number LMBP 6422CB).

2. An isolated monoclonal anti-idiotypic antibody directed against a Factor VIII human inhibitor antibody, wherein said inhibitor antibody is directed against the A2 domain of human Factor VIII, and wherein each variable region for each of the two light chains are encoded by the nucleic acid sequence set forth in SEQ ID NO: 2, and wherein each variable region of the two heavy chains of said anti-idiotypic antibody are encoded by the nucleic acid sequence set forth in SEQ ID NO: 1.

3. An isolated monoclonal anti-idiotypic antibody directed against a Factor VIII human inhibitor antibody, wherein said inhibitor antibody is directed against the A2 domain of human Factor VIII, and wherein the peptide sequence of each of the variable regions for each of the two light chains of said anti-idiotypic antibody is the sequence set forth in SEQ ID NO: 4, and wherein the peptide sequence of each of the variable regions for each of the two heavy chains of said anti-idiotypic antibody is the sequence set forth in SEQ ID NO: 3.

4. The isolated monoclonal anti-idiotypic antibody of claim 2, wherein said anti-idiotypic antibody is a mouse antibody.

5. The isolated monoclonal anti-idiotypic antibody of claim 4, wherein said anti-idiotypic antibody is a IgG1kappa antibody.

6. A F(ab')$^2$ fragment, Fab' fragment, or Fab fragment, of the isolated monoclonal anti-idiotypic antibody of claim 2 or claim 3.

7. The isolated monoclonal anti-idiotypic antibody according to claim 2, wherein said anti-idiotypic antibody is produced by the 30D1 hybridoma deposited under the accession number CNCM I-3450 at the Collection Nationale de Cultures de Microorganismes (CNCM).

8. A 30D1 hybridoma deposited under the accession number CNCM I-3450 at the Collection Nationale de Cultures de Microorganisms (CNCM).

9. An isolated DNA molecule comprising the nucleic acid sequence set forth in SEQ ID NO: 1.

10. An isolated DNA molecule comprising the nucleic acid sequence set forth in SEQ ID NO: 2.

11. A pharmaceutical composition comprising a first anti-idiotypic monoclonal antibody according to claim 2 and at least one pharmaceutically acceptable excipient and/or at least one pharmaceutically acceptable vehicle.

12. The composition of claim 11, further comprising a second anti-idiotypic monoclonal antibody directed against a domain of human Factor VIII other than the A2 domain.

13. The composition according to claim 12, wherein said second anti-idiotypic monoclonal antibody is directed against the C2 domain of human Factor VIII.

* * * * *

SEQUENCE LISTING

```
<160> NUMBER OF SEQ ID NOS: 8

<210> SEQ ID NO 1
<211> LENGTH: 461
<212> TYPE: DNA
<213> ORGANISM: Mus musculus

<400> SEQUENCE: 1
atggaatgga gctggatcat tctcttcctc ctgtcaggaa ctgcaggtgt ccactctgag      60
gtccagctgc aacagtctgg acctgagctg gtgaagcctg gagcttcaat gaagatatcc     120
tgcaaggctt ctggttactc attcactgac tacaccatga actgggtgaa gcagagccat     180
ggaaagaacc ttgagtggat tggacttatt aatccttaca atgttatttc ttcctacaac     240
cagaagttca agggcaaggc cacattaact gtagacaagt catccagcac agcctacatg     300
gagctcctca gtctgacatc tgaggactct gcagtctatt actgtgcaag aaagggctac     360
ggtagtagca tgtttgctta ctggggccaa gggactctgg tcactgtctc tgcagccaaa     420
acgacacccc catctgtcta tccactggcc cctgggtctg a                         461

<210> SEQ ID NO 2
<211> LENGTH: 431
<212> TYPE: DNA
<213> ORGANISM: Mus musculus

<400> SEQUENCE: 2
atggagtcac atactcaggt cttcgtattc gtgtttctct ggttgtctgg tgttgacgga      60
gacattgtga tgacccagtc tcacaaattc atgtccacat cagtaggagg cagggtcagc     120
atcacctgca aggccagtca ggatgtaact actgctgtag cctggtatca acagaaacca     180
ggacaatctc ctaaactact gatttactcg gcatcctacc ggtacactgg agtccctgat     240
cgcttcactg gcagtggatc tgggacggat ttcactttca ccttcagcag tgtgcaggct     300
```

-continued

```
gaagacctgg cagtttatta ctgtcagcaa cattatagta ttccgtggac gttcggtgga    360
ggcaccaagc tggaaatcaa acgggctgat gctgcaccaa ctgtatccat cttcccacca    420
tccagtgcgc a                                                         431
```

```
<210> SEQ ID NO 3
<211> LENGTH: 153
<212> TYPE: PRT
<213> ORGANISM: Mus musculus

<400> SEQUENCE: 3

Met Glu Trp Ser Trp Ile Ile Leu Phe Leu Leu Ser Gly Thr Ala Gly
1               5                   10                  15

Val His Ser Glu Val Gln Leu Gln Gln Ser Gly Pro Glu Leu Val Lys
            20                  25                  30

Pro Gly Ala Ser Met Lys Ile Ser Cys Lys Ala Ser Gly Tyr Ser Phe
        35                  40                  45

Thr Asp Tyr Thr Met Asn Trp Val Lys Gln Ser His Gly Lys Asn Leu
    50                  55                  60

Glu Trp Ile Gly Leu Ile Asn Pro Tyr Asn Val Ile Ser Ser Tyr Asn
65                  70                  75                  80

Gln Lys Phe Lys Gly Lys Ala Thr Leu Thr Val Asp Lys Ser Ser Ser
                85                  90                  95

Thr Ala Tyr Met Glu Leu Leu Ser Leu Thr Ser Glu Asp Ser Ala Val
            100                 105                 110

Tyr Tyr Cys Ala Arg Lys Gly Tyr Gly Ser Ser Met Phe Ala Tyr Trp
        115                 120                 125

Gly Gln Gly Thr Leu Val Thr Val Ser Ala Ala Lys Thr Thr Pro Pro
    130                 135                 140

Ser Val Tyr Pro Leu Ala Pro Gly Ser
145                 150
```

```
<210> SEQ ID NO 4
<211> LENGTH: 143
<212> TYPE: PRT
<213> ORGANISM: Mus musculus

<400> SEQUENCE: 4

Met Glu Ser His Thr Gln Val Phe Val Phe Val Phe Leu Trp Leu Ser
1               5                   10                  15

Gly Val Asp Gly Asp Ile Val Met Thr Gln Ser His Lys Phe Met Ser
            20                  25                  30

Thr Ser Val Gly Gly Arg Val Ser Ile Thr Cys Lys Ala Ser Gln Asp
        35                  40                  45

Val Thr Thr Ala Val Ala Trp Tyr Gln Gln Lys Pro Gly Gln Ser Pro
    50                  55                  60

Lys Leu Leu Ile Tyr Ser Ala Ser Tyr Arg Tyr Thr Gly Val Pro Asp
65                  70                  75                  80

Arg Phe Thr Gly Ser Gly Ser Gly Thr Asp Phe Thr Phe Thr Phe Ser
                85                  90                  95

Ser Val Gln Ala Glu Asp Leu Ala Val Tyr Tyr Cys Gln Gln His Tyr
            100                 105                 110

Ser Ile Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Ala
    130                 135                 140
```

<210> SEQ ID NO 5
<211> LENGTH: 1392
<212> TYPE: DNA
<213> ORGANISM: Homo sapiens

<400> SEQUENCE: 5

| | | |
|---|---|---|
| atgaaacacc tgtggttctt ccttctcctg gtggcagctc ccagatgtgt cctgtcccag | 60 |
| gtgcagctgc aggagtcggg cccaggactg gtgaagcctt cggagaccct gtccctcacc | 120 |
| tgcactgtct ctggtgactc catcagtgat tactactgga gctggatccg gcagccccca | 180 |
| gggaagggac tggagtggat tggctatttt ttttacagtg ggggcagcaa ttacaacccc | 240 |
| tccctcaaga gtcgagtcac catgtcagta gacacatcca agaaccagtt ctccctgaag | 300 |
| ctgggctctg tgaccgctgc ggacacggcc gtctattact gtgcgagatc gcagttacga | 360 |
| tattacctgg acgtctgggg ccaagggacc acggtcaccg tctcctcggc ctccaccaag | 420 |
| ggcccatcgg tcttcccccct ggcgccctgc tccaggagca cctccgagag cacagcggcc | 480 |
| ctgggctgcc tggtcaagga ctacttcccc gaaccggtga cggtgtcgtg aactcaggc | 540 |
| gccctgacca gcggcgtgca caccttcccg gctgtcctac agtcctcagg actctactcc | 600 |
| ctcagcagcg tggtgaccgt gccctccagc agcttgggca cgaagaccta cacctgcaat | 660 |
| gtagatcaca agcccagcaa caccaaggtg gacaagagag ttgagtccaa atatggtccc | 720 |
| ccatgcccat catgcccagc acctgagttc ctggggggac catcagtctt cctgttcccc | 780 |
| ccaaaaccca aggacactct catgatctcc cggacccctg aggtcacgtg cgtggtggtg | 840 |
| gacgtgagcc aggaagaccc cgaggtccag ttcaactggt acgtggatgg cgtggaggtg | 900 |
| cataatgcca agacaaagcc gcgggaggag cagttcaaca gcacgtaccg tgtggtcagc | 960 |
| gtcctcaccg tcctgcacca ggactggctg aacggcaagg agtacaagtg caaggtctcc | 1020 |
| aacaaaggcc tcccgtcctc catcgagaaa accatctcca aagccaaagg gcagccccga | 1080 |
| gagccacagg tgtacaccct gcccccatcc caggaggaga tgaccaagaa ccaggtcagc | 1140 |
| ctgacctgcc tggtcaaagg cttctacccc agcgacatcg ccgtggagtg ggagagcaat | 1200 |
| gggcagccgg agaacaacta caagaccacg cctcccgtgc tggactccga cggctccttc | 1260 |
| ttcctctaca gcaggctaac cgtggacaag agcaggtggc aggaggggaa tgtcttctca | 1320 |
| tgctccgtga tgcatgaggc tctgcacaac cactacacac agaagagcct ctccctgtct | 1380 |
| ctgggtaaat ga | 1392 |

<210> SEQ ID NO 6
<211> LENGTH: 699
<212> TYPE: DNA
<213> ORGANISM: Homo sapiens

<400> SEQUENCE: 6

| | | |
|---|---|---|
| atggaaaccc cagckcagct tctcttcctc ctgctactct ggctcccaga taccaccgga | 60 |
| gaaattgtgt tgacgcagtc tccaggcacc ctgtctttgt ctccagggga agagccacc | 120 |
| ctctcctgca gggccagtca gagtgttgac agcaactact tagcctggta ccagcagaaa | 180 |
| cctggccagg ctcccagggt cgtcatctat ggtgcatcca cagggccac tggcatccca | 240 |
| gacaggttca gtggcagtgg gtctgggaca gagttcactc tcaccatcag cagactggac | 300 |
| cctgaagatt ttgcagtgta ttactgtcag cagtatggta gcttcttcgg ccaagggaca | 360 |
| cgactggaga ttaaacgaac tgtggctgca ccatctgtct tcatcttccc gccatctgat | 420 |
| gagcagttga aatctggaac tgcctctgtt gtgtgcctgc tgaataactt ctatcccaga | 480 |

-continued

```
gaggccaaag tacagtggaa ggtggataac gccctccaat cgggtaactc ccaggagagt      540
gtcacagagc aggacagcaa ggacagcacc tacagcctca gcagcaccct gacgctgagc      600
aaagcagact acgagaaaca caaagtctac gcctgcgaag tcacccatca gggcctgagc      660
tcgcccgtca caaagagctt caacagggga gagtgttag                              699
```

<210> SEQ ID NO 7
<211> LENGTH: 463
<212> TYPE: PRT
<213> ORGANISM: Homo sapiens

<400> SEQUENCE: 7

```
Met Lys His Leu Trp Phe Phe Leu Leu Leu Val Ala Ala Pro Arg Cys
1               5                   10                  15

Val Leu Ser Gln Val Gln Leu Gln Glu Ser Gly Pro Gly Leu Val Lys
            20                  25                  30

Pro Ser Glu Thr Leu Ser Leu Thr Cys Thr Val Ser Gly Asp Ser Ile
        35                  40                  45

Ser Asp Tyr Tyr Trp Ser Trp Ile Arg Gln Pro Pro Gly Lys Gly Leu
    50                  55                  60

Glu Trp Ile Gly Tyr Phe Tyr Ser Gly Ser Asn Tyr Asn Pro
65                  70                  75                  80

Ser Leu Lys Ser Arg Val Thr Met Ser Val Asp Thr Ser Lys Asn Gln
                85                  90                  95

Phe Ser Leu Lys Leu Gly Ser Val Thr Ala Ala Asp Thr Ala Val Tyr
            100                 105                 110

Tyr Cys Ala Arg Ser Gln Leu Arg Tyr Tyr Leu Asp Val Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val Glu Ser Lys Tyr Gly Pro
225                 230                 235                 240

Pro Cys Pro Ser Cys Pro Ala Pro Glu Phe Leu Gly Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
```

```
                340                 345                 350
Ser Lys Ala Lys Gly Gln Pro Arg Glu Pro Gln Val Tyr Thr Leu Pro
            355                 360                 365
Pro Ser Gln Glu Glu Met Thr Lys Asn Gln Val Ser Leu Thr Cys Leu
        370                 375                 380
Val Lys Gly Phe Tyr Pro Ser Asp Ile Ala Val Glu Trp Glu Ser Asn
385                 390                 395                 400
Gly Gln Pro Glu Asn Asn Tyr Lys Thr Thr Pro Pro Val Leu Asp Ser
                405                 410                 415
Asp Gly Ser Phe Phe Leu Tyr Ser Arg Leu Thr Val Asp Lys Ser Arg
            420                 425                 430
Trp Gln Glu Gly Asn Val Phe Ser Cys Ser Val Met His Glu Ala Leu
        435                 440                 445
His Asn His Tyr Thr Gln Lys Ser Leu Ser Leu Ser Leu Gly Lys
    450                 455                 460

<210> SEQ ID NO 8
<211> LENGTH: 232
<212> TYPE: PRT
<213> ORGANISM: Homo sapiens

<400> SEQUENCE: 8

Met Glu Thr Pro Ala Gln Leu Leu Phe Leu Leu Leu Leu Trp Leu Pro
1               5                   10                  15
Asp Thr Thr Gly Glu Ile Val Leu Thr Gln Ser Pro Gly Thr Leu Ser
            20                  25                  30
Leu Ser Pro Gly Glu Arg Ala Thr Leu Ser Cys Arg Ala Ser Gln Ser
        35                  40                  45
Val Asp Ser Asn Tyr Leu Ala Trp Tyr Gln Gln Lys Pro Gly Gln Ala
    50                  55                  60
Pro Arg Val Val Ile Tyr Gly Ala Ser Asn Arg Ala Thr Gly Ile Pro
65                  70                  75                  80
Asp Arg Phe Ser Gly Ser Gly Ser Gly Thr Glu Phe Thr Leu Thr Ile
                85                  90                  95
Ser Arg Leu Asp Pro Glu Asp Phe Ala Val Tyr Tyr Cys Gln Gln Tyr
            100                 105                 110
Gly Ser Phe Phe Gly Gln Gly Thr Arg Leu Glu Ile Lys Arg Thr Val
        115                 120                 125
Ala Ala Pro Ser Val Phe Ile Phe Pro Pro Ser Asp Glu Gln Leu Lys
    130                 135                 140
Ser Gly Thr Ala Ser Val Val Cys Leu Leu Asn Asn Phe Tyr Pro Arg
145                 150                 155                 160
Glu Ala Lys Val Gln Trp Lys Val Asp Asn Ala Leu Gln Ser Gly Asn
                165                 170                 175
Ser Gln Glu Ser Val Thr Glu Gln Asp Ser Lys Asp Ser Thr Tyr Ser
            180                 185                 190
Leu Ser Ser Thr Leu Thr Leu Ser Lys Ala Asp Tyr Glu Lys His Lys
        195                 200                 205
Val Tyr Ala Cys Glu Val Thr His Gln Gly Leu Ser Ser Pro Val Thr
    210                 215                 220
Lys Ser Phe Asn Arg Gly Glu Cys
225                 230
```